United States Patent
Wu et al.

(10) Patent No.: US 8,404,842 B2
(45) Date of Patent: *Mar. 26, 2013

(54) ORGANIC AND INORGANIC PHOTOSENSITIZER DYES

(75) Inventors: Chn-Guey Wu, Hualien (TW);
Jheng-Ying Li, Jhongli (TW);
Chia-Yuna Chen, Chiayi (TW);
Shi-Jhang Wu, Luzhou (TW)

(73) Assignee: National Central University, Jhongli (TW)

( * ) Notice: Subject to any disclaimer, the term of this patent is extended or adjusted under 35 U.S.C. 154(b) by 190 days.

This patent is subject to a terminal disclaimer.

(21) Appl. No.: 12/924,777

(22) Filed: Oct. 5, 2010

(65) Prior Publication Data

US 2011/0288300 A1    Nov. 24, 2011

(30) Foreign Application Priority Data

May 19, 2010    (TW) .............................. 99116022 A

(51) Int. Cl.
*C07F 15/00*    (2006.01)
*H01L 31/00*    (2006.01)
(52) U.S. Cl. ............................. 546/2; 136/263; 136/252
(58) Field of Classification Search ...... 546/2; 136/263, 136/252

See application file for complete search history.

(56) References Cited

U.S. PATENT DOCUMENTS

| | | | | |
|---|---|---|---|---|
| 7,321,037 B2 * | 1/2008 | Wu et al. | ......................... | 546/10 |
| 7,645,879 B2 * | 1/2010 | Wu et al. | ......................... | 546/2 |
| 8,143,399 B2 * | 3/2012 | Wu et al. | ......................... | 546/2 |
| 8,188,278 B2 * | 5/2012 | Tung et al. | ......................... | 546/2 |

OTHER PUBLICATIONS

Chen, C-Y et al. : Multifunctionalized Ruthenium-based supersensitizers for highly efficient dye-sensitized solar cells. Angew. Chem. Int. Ed. vol. 47, pp. 7342-7345, 2008.*

Chen, C-Y. et al.: New Ruthenium sensitizer with carbazole antennas for efficient and stable thin-film dye-sensitized solar cells. J. Phys. Chem. vol. 113, pp. 20752-20757, 2009.*

* cited by examiner

*Primary Examiner* — Charanjit Aulakh
(74) *Attorney, Agent, or Firm* — Hudak, Shunk & Farine Co. LPA

(57) ABSTRACT

The present invention discloses organic and inorganic photosensitizer dyes as the following formulas (1) to (3), wherein the substituents "A, B, D and G" are as defined in claim 1.

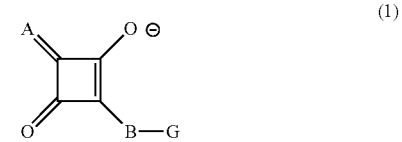

(1)

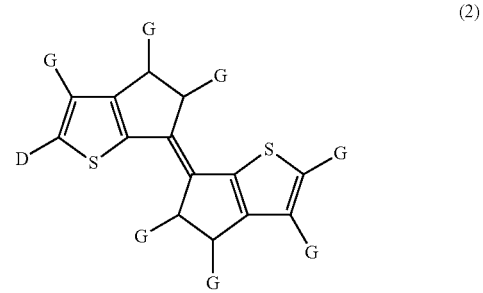

(2)

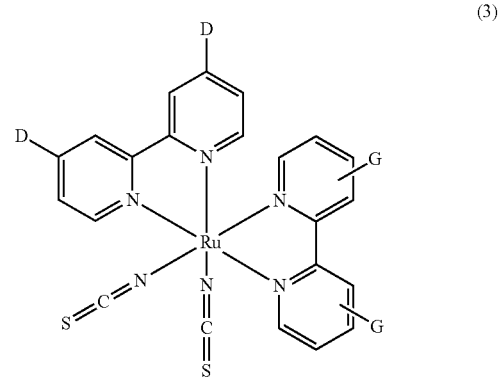

(3)

4 Claims, 4 Drawing Sheets

ORGANIC AND INORGANIC PHOTOSENSITIZER DYES

FIELD OF THE INVENTION

The present invention relates to the photosensitizer dyes, and more particularly, to the organic and inorganic photosensitizer dyes.

BACKGROUND OF THE INVENTION

"Energy" has become one of the important issues to be developed and resolved, recently. Thus, many countries have started to develop and invest in renewable energy sources. Solar energy is an unlimited and non-polluting energy source; furthermore, the development and application of the solar energy are not limited by the topography, geomorphology or other relating factors; therefore solar energy becomes one of the most important renewable energies. Solar energy can be directly converted to commonly used electricity by an appropriate equipment or device. An equipment or device converting the solar energy to electricity is called a solar cell.

Recently, a new type of the solar cells known as dye-sensitized solar cells (DSCs), has been proposed by the Switzerland professor, Micheal Grätzel. Dye-sensitized solar cells have many advantages, such as a low manufacturing cost, good photoelectric conversion efficiency, high transparency, colorfulness, flexibility, and etc.; therefore dye-sensitized solar cells have been concerned in the industry application. Generally, a dye-sensitized solar cell is constituted with four major components: an anode/cathode for providing a channel of the current flow, a semiconducting material such as $TiO_2$ or ZnO for accepting and transporting electrons, a dye layer adsorbed on the surface of the semiconducting material via self-assembly, and an electrolyte for transforming electronic holes. The materials and the interfaces between each component of the dye-sensitized solar cells play important roles on the conversion efficiency of the device. Most particularly, photosensitizer dyes are critical in determining the efficiency of the dye-sensitized solar cells. Thus, searching for the high efficiency photosensitizer dyes has become one of the most active research activities in the past two decades.

SUMMARY OF THE INVENTION

In view of the aforementioned drawbacks in prior art, an object of the present invention is to provide organic and inorganic photosensitizer dyes. The photosensitizer dyes of the present invention have high absorption coefficient, and the absorption spectrum of the photosensitizer dyes is more close to that of the sunlight. Some of the organic molecules can absorb far-red light effectively and therefore the dye-sensitized solar cells based on the photosensitizer dyes of the present invention will have good conversion efficiency.

The present invention provides a series organic and inorganic photsensitizer dyes, and the formulas thereof are represented as following formulas (1) to (3):

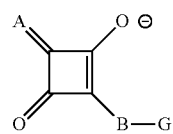

(1)

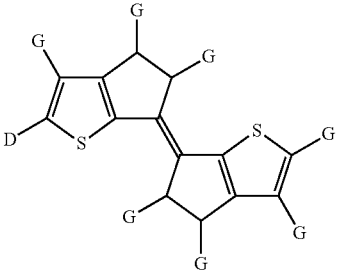

(2)

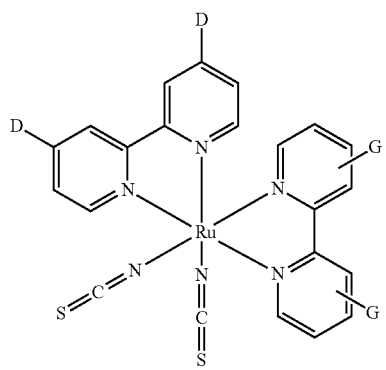

(3)

wherein "A" in the formula (1) represents one of the following formulas (4) to (15).

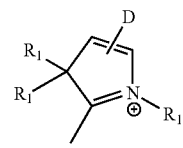

(4)

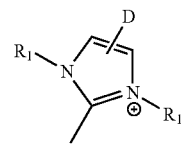

(5)

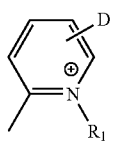

(6)

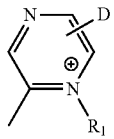

(7)

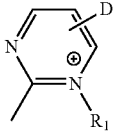

(8)

(9) 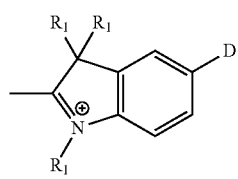
(10) 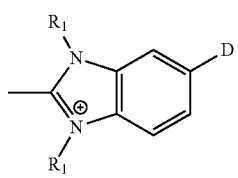
(11) 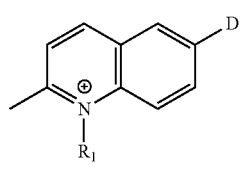
(12) 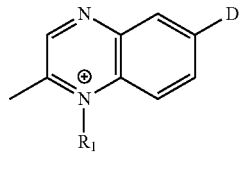
(13) 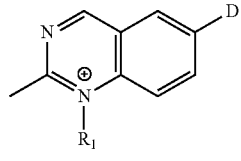
(14) 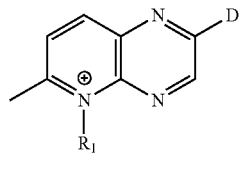
(15) 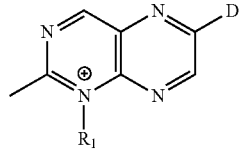
$R_1$ independently represents $-C_xH_{2x+1}$, $-(C_yH_{2y})-OC_xH_{2x+1}$, $-(C_yH_{2y})-SC_xH_{2x+1}$, $-(C_yH_{2y})-N(C_xH_{2x+1})_2$ (x=1 to 20; y=1 to 20) or one of formulas (49) to (50). "B" in the formula (1) represents one of formulas (16) to (42) or the combination of formulas (16) to (42).
(16) 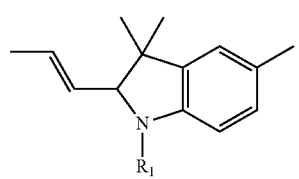
(17) 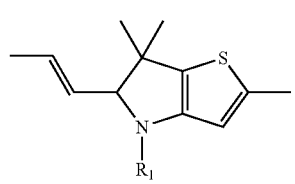
(18) 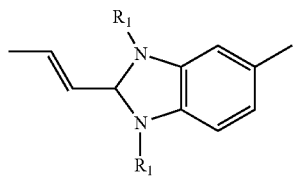
(19) 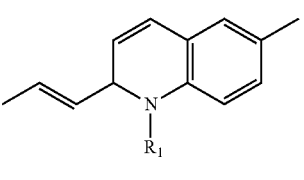
(20) 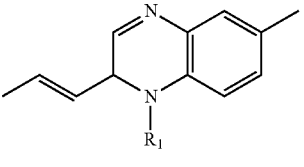
(21) 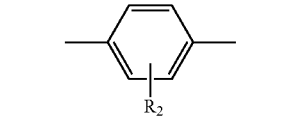
(22) 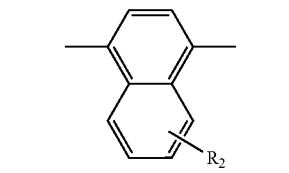
(23) 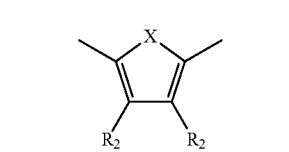
(24) 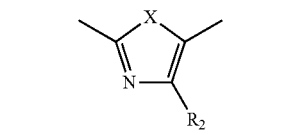
(25) 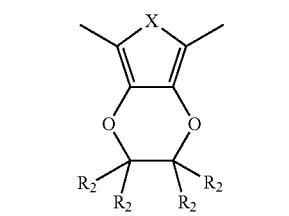

(26) 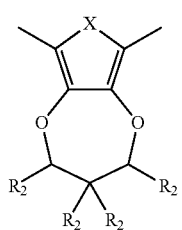
(27) 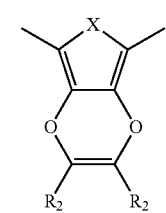
(28) 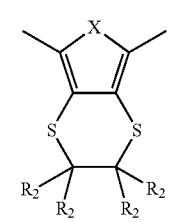
(29) 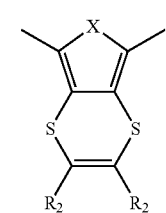
(30) 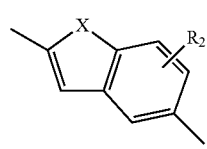
(31) 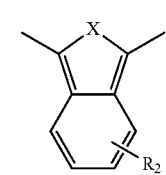
(32) 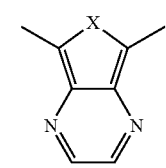
(33) 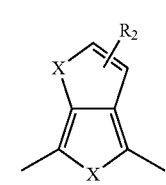
(34) 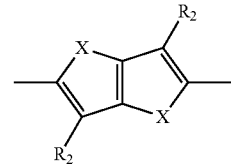
(35) 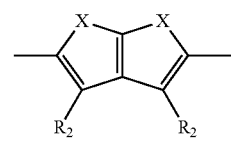
(36) 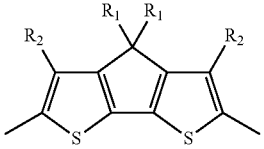
(37) 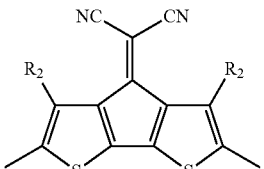
(38) 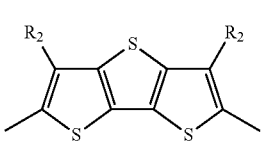
(39) 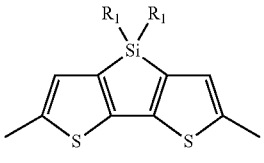
(40) 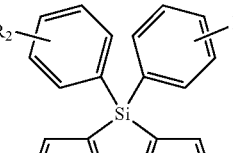
(41) 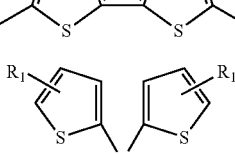
(42) 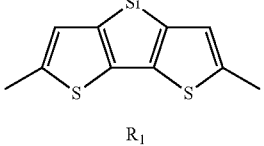
$R_1$ in the formulas (16) to (20), (36), (39), (41) and (42) represents independently one of —$C_xH_{2x+1}$, —$(C_yH_{2y})$—

$OC_xH_{2x+1}$, $-(C_yH_{2y})-SC_xH_{2x+1}$, $-(C_yH_{2y})-N(C_xH_{2x+1})_2$ (x=1 to 20; y=1 to 20) or formulas (49) to (50). $R_2$ in the formulas (21) to (31), (33) to (38) and (40) represents independently one of hydrogen (—H), $-C_xH_{2x+1}$, $-(C_zH_{2z})-OC_xH_{2x+1}$, $-(C_zH_{2z})-SC_xH_{2x+1}$, $-(C_zH_{2z})-N(C_xH_{2x+1})_2$ (x=1 to 20; z=0 to 20) or formulas (48) to (50). Briefly, "X" in the formulas (23) to (35) independently represents one of sulfur (S), an amino group (N—R; R represents $C_qH_{2q+1}$ (q=1 to 20)), oxygen (O) or selenium (Se).

"G" in the formulas (1) to (3) represents independently one of formulas (43) to (73).

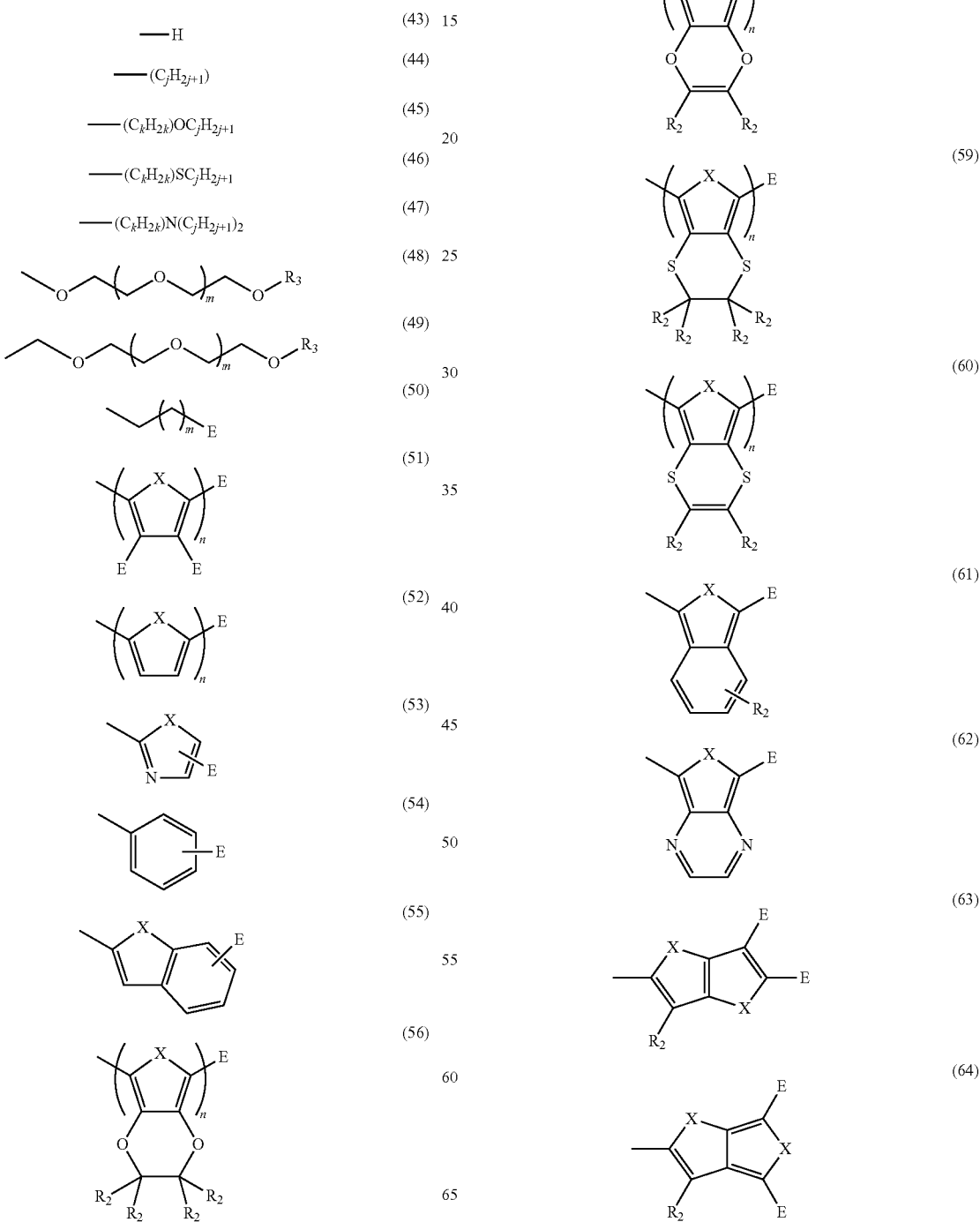

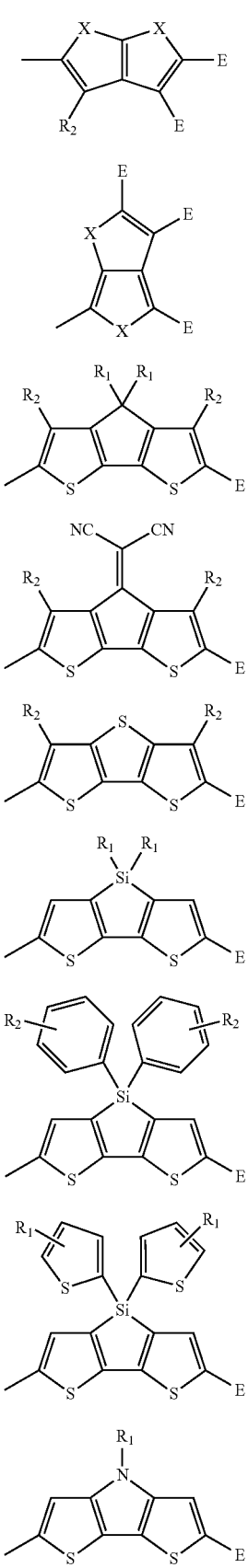

$R_1$ in the formulas (67), (70), (72) and (73) represents independently one of $-C_xH_{2x+1}$, $-(C_yH_{2y})-OC_xH_{2x+1}$, $-(C_yH_{2y})-SC_xH_{2x+1}$, $-(C_yH_{2y})-N(C_xH_{2x+1})_2$ (x=1 to 20; y=1 to 20), the formula (49) or the formula (50). $R_2$ in the formulas (56) to (61), (63) to (69) and (71) represents independently one of hydrogen (—H), $-C_xH_{2x+1}$, $-(C_zH_{2z})-OC_xH_{2x+1}$, $-(C_zH_{2z})-SC_xH_{2x+1}$, $-(C_zH_{2z})-N(C_xH_{2x+1})_2$ (x=1 to 20; z=0 to 20) or formulas (48) to (50). $R_3$ in the formulas (48) and (49) represents independently one of hydrogen (—H) or $-C_xH_{2x+1}$ (x=1 to 20). Briefly, "X" in the formulas (51) to (53), and (55) to (66) represents independently sulfur (S), an amino group (N—R; R represents $C_qH_{2q+1}$ (q=1 to 20)), oxygen (O) or selenium (Se); j=1 to 20 in the formulas (44) to (47); k=0 to 20 in the formulas (45) to (47); m=0 to 10 in the formulas (48) to (50); and n=0 to 4 in the formulas (51) to (52) and (56) to (60).

"D" in the formulas (2) to (15) represents independently one of following formulas (74) to (83).

 (74)

 (75)

 (76)

 (77)

 (78)

 (79)

 (80)

 (81)

 (82)

 (83)

"E" in the formulas (50) to (73) represents independently one of formulas (43) to (49) or (84) to (97). "G" in the formula (79), (81) and (83) is the same with the aforementioned description, and thus not repeated again herein.

-continued

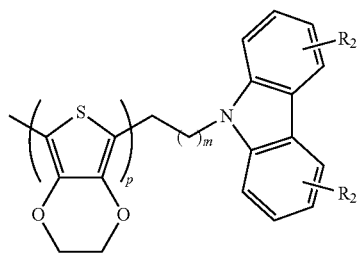
(97)

$R_1$ in the formulas (87), (93) and (94) represents independently $-C_xH_{2x+1}$, $-(C_yH_{2y})-OC_xH_{2x+1}$, $-(C_yH_{2y})-SC_xH_{2x+1}$, $-(C_yH_{2y})-N(C_xH_{2x+1})_2$ (x=1 to 20; y=1 to 20) or one of formulas (49) to (50). $R_2$ in the formulas (84) to (97) represents independently one of hydrogen (—H), $-C_xH_{2x+1}$, $-(C_zH_{2z})-OC_xH_{2x+1}$, $-(C_zH_{2z})-SC_xH_{2x+1}$, $-(C_zH_{2z})-N(C_xH_{2x+1})_2$ (x=1 to 20; z=0 to 20) or formulas (48) to (50). $R_4$ in the formula (91) represents independently $C_wH_{2w}$ (w=1 to 2). Briefly, in the formulas (84) to (97), m=0 to 10 and p=0 to 2.

"Z" in the formulas (74) to (83) represents independently hydrogen (H), lithium (Li), sodium (Na), potassium (K) or a quaternary ammonium salt (as shown in the following formula (98)).

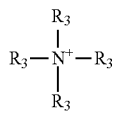
(98)

$R_3$ in the formula (98) represents independently one of hydrogen (—H) or $-C_xH_{2x+1}$ (x=1 to 20).

In the formula (1), when "D" in one of the formulas (4) to (15) (represented as "A") represents the formula (74), "B" represents one of the formulas (21) to (24) or (30) to (32), "G" represents one of the formulas (51) to (55) or (61) to (62), and "E" in the formulas (51) to (55) or (61) to (62) represents the formula (84), m≠0 in the formula (84). In other words, the following formula (99) is not represented in the present invention.

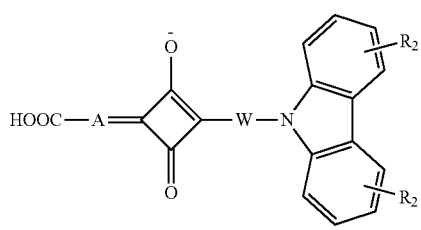
(99)

In the formula (99), "A" represents one of the formulas (4) to (15) and "W" represents one or the combination of formulas (100) to (107).

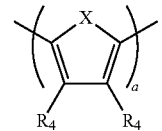
(100)

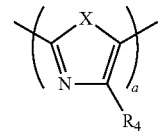
(101)

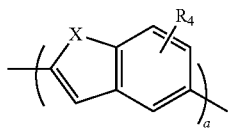
(102)

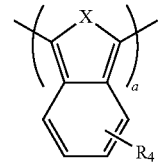
(103)

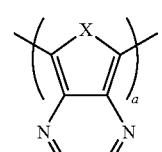
(104)

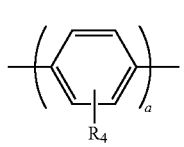
(105)

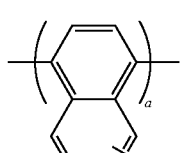
(106)

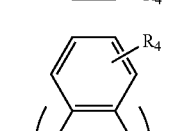
(107)

"X" represents in the formulas (100) to (104) independently one of sulfur (S), an amino group (N—R; R represents $C_qH_{2q+1}$ (q=1 to 20)), oxygen (O) or selenium (Se). In the formulas (100) to (107), a=1 to 4 and $R_4$ represents independently one of hydrogen (—H), $-C_xH_{2x+1}$, $-(C_zH_{2z})-OC_xH_{2x+1}$, $-(C_zH_{2z})-SC_xH_{2x+1}$ or $-(C_zH_{2z})-N(C_xH_{2x+1})_2$ (x=1 to 20; z=0 to 20).

In the formula (1), when "A" represents one of the formulas (6) to (9) or one of the formulas (11) to (13), "D" in the formulas (6) to (9) or (11) to (13) represents one of the formulas (76) to (78), and "Z" in the formulas (76) to (78)

represents H, "B" dose not represent the formula (16) and "G" does not represent one of the formulas (43) to (47). In the meanwhile, when "G" represents one of the formulas (51) to (55), "E" in the formulas (51) to (55) does not represent one of the formulas (43) to (47). When "E" represents the formulas (84), (88) or (89), m≠0 in the formulas (84), (88) or (89). In other words, the following formula (108) is not represented in the present invention.

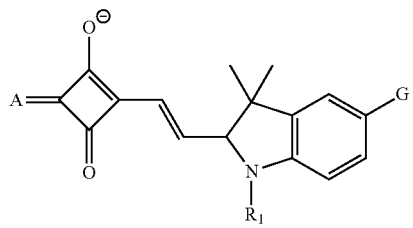

(108)

"A" in the formula (108) represents one of the formulas (6) to (9) or (11) to (13), D in the formulas (6) to (9) or (11) to (13) represents one of the formulas (76) to (78), and "Z" in the formulas represents H. "G" in formula (108) represents one of the formulas (43) to (47) or formula (51) to (55) and E in the formulas (51) to (55) represents one of the formulas (43) to (47), (84) or (85), and m=0 in the formulas (84) to (85).

In the formula (3), when "D" represents one of the formulas (74) to (76) or (79) to (82) and "G" represents one of the formulas (51) to (66), "E" in the formulas (51) to (66) does not represent one of the formulas (43) to (49). In the meanwhile, when "E" in the formulas (51) to (66) represents one of the formulas (84) to (95), m≠0 in the formulas (84) to (95). For example, the following formula (109) is not represented in the present invention.

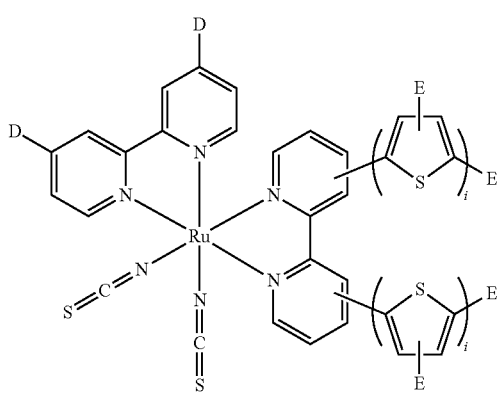

(109)

Wherein i=1 to 3 in the formula (109). "D" represents one of the formulas (74) to (76) or (79) to (82). "E" represents one of the formulas (43) to (49) or (84) to (95), and m=0 in the formulas (84) to (95).

When "D" in the formula (3) represents one of the formulas (77) or (78) and "Z" in the formulas (77) or (78) represents H, "G" in the formula (3) do not represent one of the formulas (43) to (47). In the meanwhile, when "G" represents one of the formulas (51) to (55) and "E" in the formulas (51) to (55) represents one of the formulas (84), (88) or (89), m≠0 in the formulas (84), (88) or (89). In other words, the following formulas (110) and (111) do not be represented in the present invention.

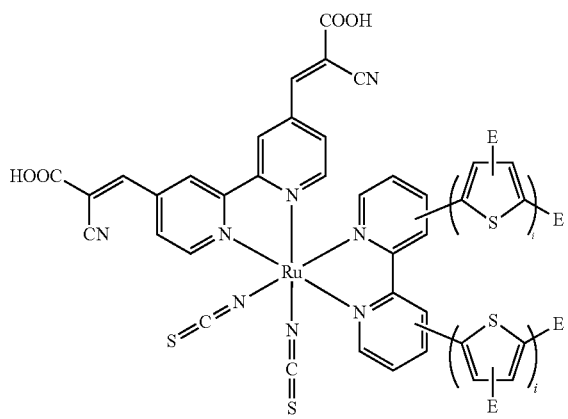

(110)

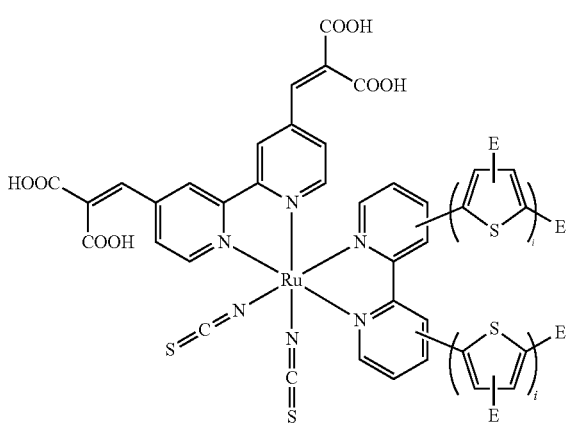

(111)

Wherein i=1 to 3 in the formulas (110) and (111) independently. "E" represents independently one of the formulas (43) to (47), (84), (88) or (89), and m=0 in the formulas (84), (88) and (89).

A series of the organic and inorganic photosensitizer dyes with the formulas (1) to (3) according to the present invention, have the specific groups as set forth. That is, "A" represents one of the formulas (4) to (15); "B" represents one of the formulas (16) to (42); G represents independently one of the formulas (43) to (73); "D" represents independently one of the formulas (74) to (83); and "E" represents independently one of the formulas (43) to (49) or (84) to (97). Thus, the series of the organic and inorganic photosensitizer dyes according to the present invention have good light absorption capacity and high molar absorption coefficient (ε). In other words, the organic and inorganic photosensitizer dyes according to the present invention can effectively absorb the photons of the visible light and the parts of the near infrared light in sunlight. The absorption properties for parts of the organic and inorganic photosensitizer dyes of the present invention will be further described in detail in the following.

Additionally, the energy levels of the organic and inorganic photosensitizer dyes in the present invention can match well with both of the oxidation potential of the cathode and the conduction band of the anode in a normal dye-sensitized solar cell; therefore the dye-sensitized solar cells based on these dyes have high efficiency for conversing sunlight to electricity.

In parts of the embodiments, the structures of the photosensitizer dyes of the present invention are shown in formulas (112) to (119) as following:

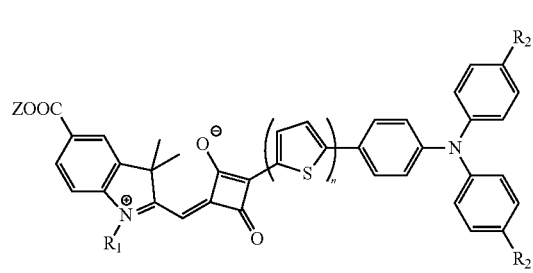
(112)
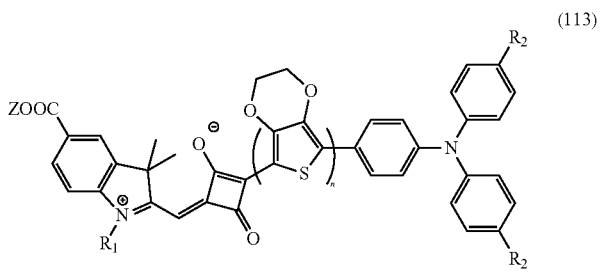
(113)
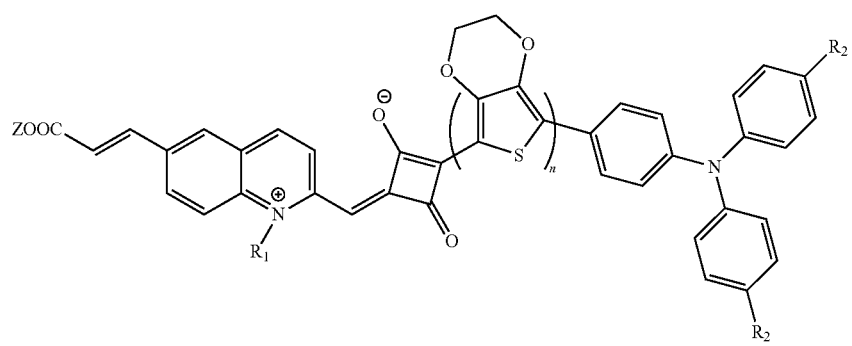
(114)
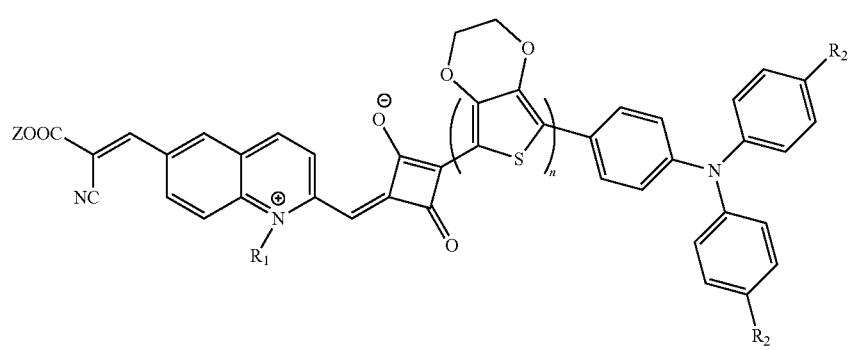
(115)
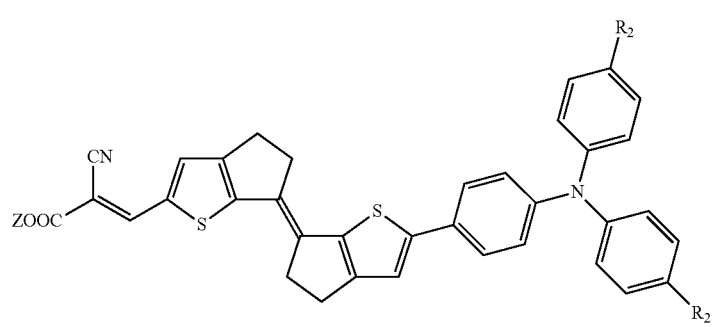
(116)
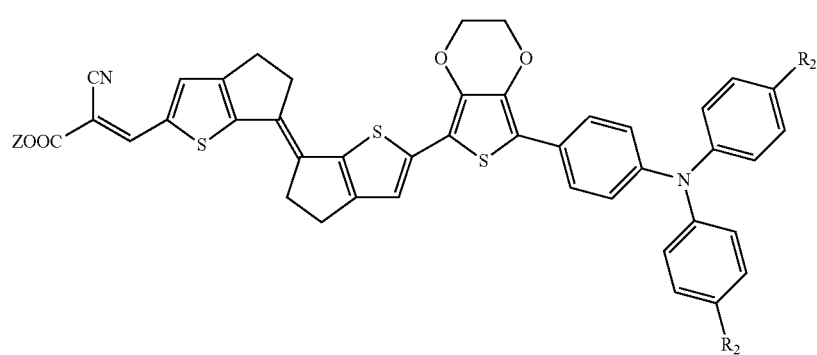
(117)

-continued

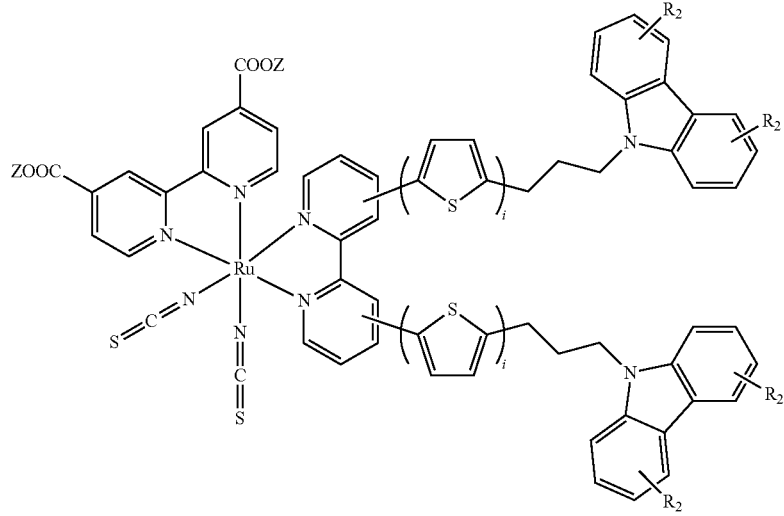

(118)

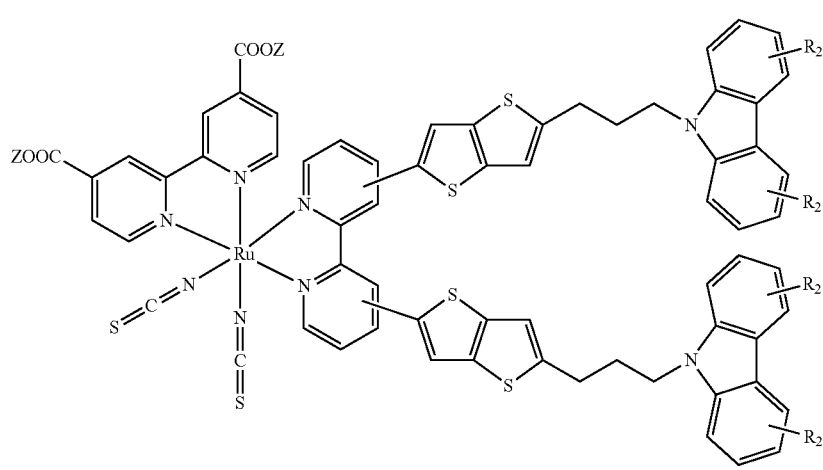

(119)

Wherein n=0 to 4 in the formulas (112) to (115) independently; and i=1 to 3 in the formula (118) independently. $R_1$ in the formulas (112) to (115) represents independently one of $-C_xH_{2x+1}$, $-(C_yH_{2y})-OC_xH_{2x+1}$, $-(C_yH_{2y})-SC_xH_{2x+1}$, $-(C_yH_{2y})-N(C_xH_{2x+1})_2$ (x=1~20; y=1~20) or the formulas (49) to (50). $R_2$ in the formulas (112) to (115) represents independently one of H, $-C_xH_{2x+1}$, $-(C_zH_{2z})-(C_xH_{2x+1})$, $-(C_zH_{2z})-SC_xH_{2x+1}$, $-(C_zH_{2z})-N(C_xH_{2x+1})_2$ (x=1~20; z=0~20) or the formulas (48) to (50). "Z" in the formulas (112) to (115) represents independently H, lithium (Li), sodium (Na), potassium (K) or the quaternary ammonium salt as shown in the formula (98).

The following embodiment describes the synthesis of the organic and inorganic photosensitizer dyes of the present invention. It should be appreciated that the following description should be regarded as illustration rather than restriction.

BRIEF DESCRIPTION OF THE DRAWINGS

The structure and the technical terms adopted by the present invention to achieve the above and other objects can be best understood by referring to the following detailed description of the preferred embodiments and the accompanying drawings, wherein.

DETAILED DESCRIPTION OF THE PREFERRED EMBODIMENTS

The First Synthesis Example

Figure 1:
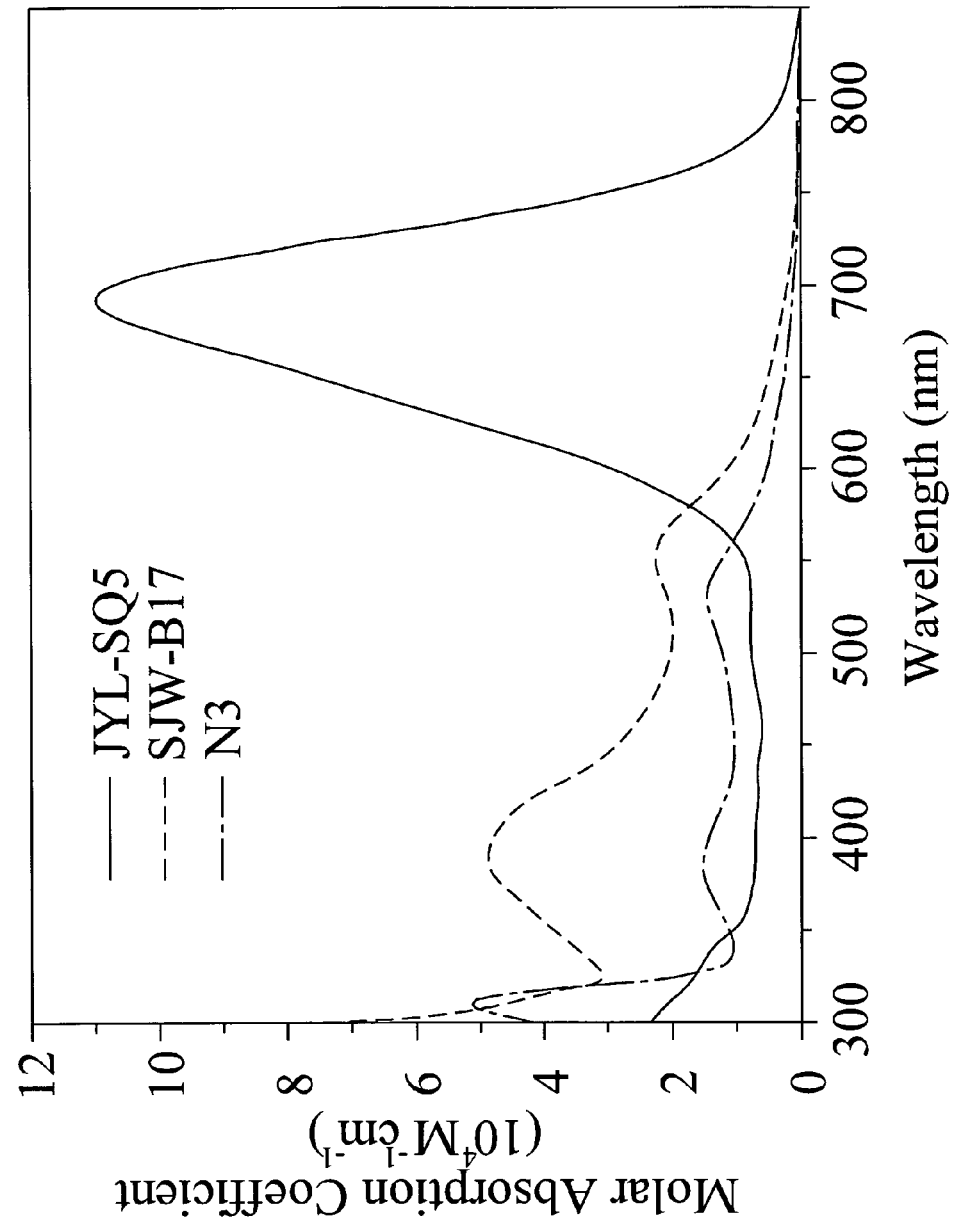
FIG. 1 is the absorption spectra of the photosensitizer dyes (JYL-SQ5 and SJW-B17) of the present invention and the photosensitizer dye (N3) of the prior art.

Compound represented as JYL-SQ5 is used as the first example to illustrate the syntheses of a series of organic and inorganic photosensitizer dyes of the present invention.

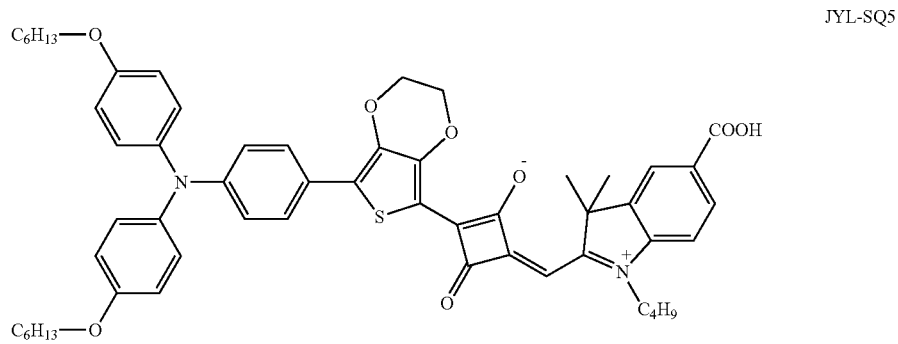

JYL-SQ5

JYL-SQ5 is a compound with a structure of the formula (1) when "A" in the formula (1) represents the formula (9), $R_1$ in the formula (9) connecting with N atom represents —$C_4H_9$, other two $R_1$ groups in the formula (9) both represent —$CH_3$, and "D" in the formula (9) represents the formula (74); "Z" in the formula (74) represents hydrogen (—H); "B" in the formula (1) represents the formula (25), wherein "X" represents sulfur (S) atom and $R_2$ represents hydrogen (—H); "G" in the formula (1) represents the formula (54), and "E" in the formula (54) represents the formula (85), wherein m=0 and p=0, and $R_2$ represents —$OC_6H_{13}$.

The synthetic scheme for preparing JYL-SQ5 is presented as the following:

Scheme 1: Synthesis of JYL-SQ5

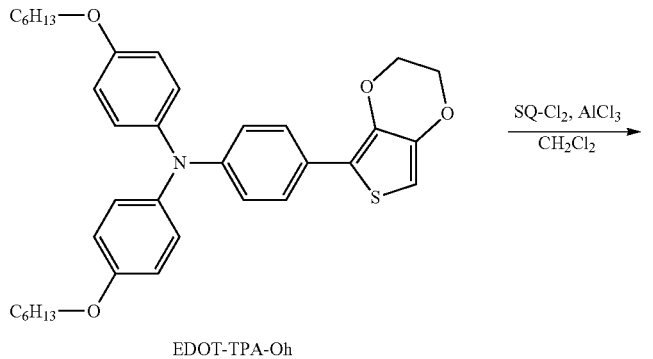

EDOT-TPA-Oh

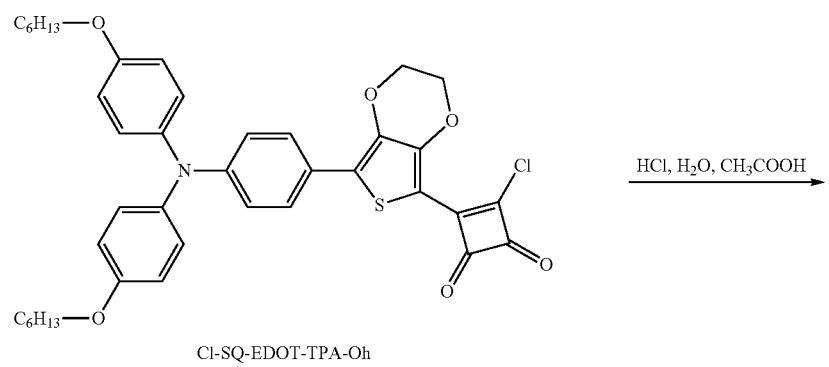

Cl-SQ-EDOT-TPA-Oh

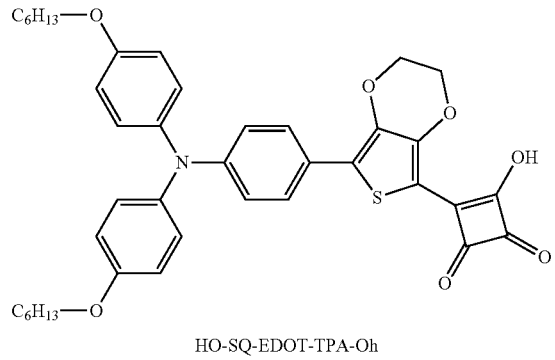
HO-SQ-EDOT-TPA-Oh

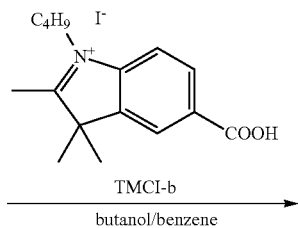
TMCl-b
butanol/benzene

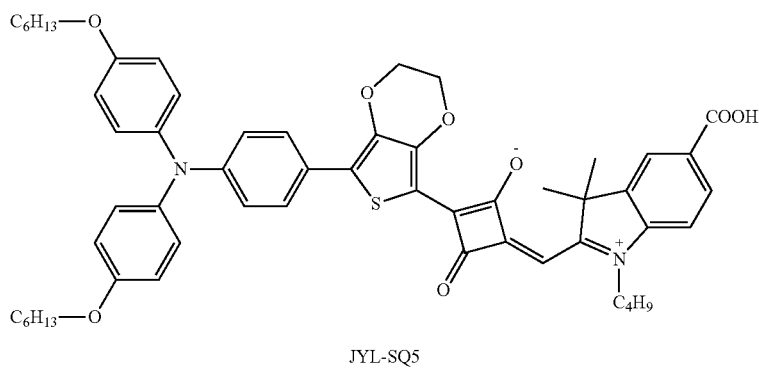
JYL-SQ5

First, 0.8 g (6 mmol) AlCl₃ and 3.51 g (6.07 mmol) EDOT-TPA-Oh (the synthesis method can be referred to G. Zhang, H. Bala, Y. Cheng, D. Shi, X. Lv, Q. Yu, P. Wang. Chem. Commun., 2009, 2198.) were put in a round-bottom flask, followed by adding 60 ml of anhydrous dichloromethane, and then a solution containing 2.26 g (15 mmol) SQ-Cl2 (3,4-dichloro-3-cyclobutene-1,2-dione; the synthesis method can be referred to M. Ohno, Y. Yamamoto, Y. Shirasaki, S. Eguchi, J. Chem. Soc., Perkin Trans. 1993, 263.) dissolved in 5 ml dichloromethane was added dropwisely under argon. The mixture was refluxed for 8 hours. After the temperature of the solution returned to the room temperature, a saturated ammonium chloride aqueous solution was added to terminate the reaction. Chloroform was used to extract the product. The organic layer was collected and washed by saturated ammonium chloride aqueous solution, de-ionized water and a saturated sodium chloride aqueous solution, respectively to remove the impurity. The organic layer was dried over anhydrous MgSO₄ and then most of the solvent was removed by a rotary evaporator. The crude product was further purified by chromatography with ethyl acetate/hexane as an eluent to obtain 0.86 g of the first intermediate (3-(5-(4-(bis(4-(hexyloxy)phenyl)amino)phenyl)-2,3-dihydro-thieno-[3,4-b][1,4]-dioxin-7-yl)-4-chloro-cyclobut-3-ene-1,2-dione), coded Cl-SQ-EDOT-TPA-Oh. ¹H-NMR (300 MHz, δ$_H$/ppm in CDCl₃): 0.92 (6H); 1.24-1.54 (12H); 1.71 (4H); 3.93 (4H); 4.34-4.46 (4H); 6.82-6.89 (6H); 7.07 (4H); 7.62 (2H).

Thereafter, 0.86 g Cl-SQ-EDOT-TPA-Oh was dissolved in a mixture of acetic acid (3.7 ml), water (3.6 ml), and 2N HCl(aq) (0.5 ml), and the mixture was refluxed for 8 hours. After the temperature of the solution returned to the room temperature, the solvent was removed under vacuum. The crude product was further purified by chromatography using chloroform/methanol as an eluent to obtain 0.51 g the second intermediate coded HO-SQ-EDOT-TPA-Oh (3-(5-(4-(bis(4-(hexyloxy)-phenyl)amino)phenyl)-2,3-di-hydrothieno[3,4-b][1,4]dioxin-7-yl)-4-hydroxycyclobut-3-ene-1,2-dione). ¹H-NMR (300 MHz, δ$_H$/ppm in CDCl₃): 0.86 (6H); 1.5-1.42 (12H); 1.63-1.71 (4H); 3.91 (4H); 4.26 (4H); 6.76 (2H); 6.88 (4H); 6.99 (4H); 7.48 (2H).

Thereafter, 1.2 g (1.76 mmol) of HO-SQ-EDOT-TPA-Oh and 1.0 g (2.6 mmol) TMCl-b (5-Carboxy-2,3,3-trimethyl-1-butyl-3H-indolium iodide (the synthesis can be referred to J. H. Yum, P. Walter, S, Huber, D. Rentsch, T. Geiger, F. Nuësch, F. D. Angelis, M. Grätzel, M. K. Nazeeruddin, J. Am. Chem. Soc., 2007, 129, 10320.) were dissolved in a mixture of 40 ml benzene and 40 ml n-butanol. Using the Dean-Stark apparatus, the mixture was refluxed under argon for 24 hours. After the temperature of the solution returned to the room temperature, the solvent was removed under vacuum. The crude product was further purified by chromatography using chloroform/methanol (40/1) as an eluent to obtain 0.25 g the final product, 5-Carboxy-2-[[3-(5-(4-(bis(4-(hexyloxy)phenyl) amino)phenyl)-2,3-dihydrothieno [3,4-b][1,4]dioxin-7-yl)-2-hydroxy-4-oxo-2-cyclobuten-1-ylidene]methyl]-3,3-dimethyl-1-butyl-3H-indolium (coded JYL-SQ5). $^1$H-NMR (300 MHz, $\delta_H$/ppm in DMSO-d6): 0.89 (9H); 1.28-1.39 (15H); 1.66-1.71 (11H); 3.92 (4H); 4.25-4.41 (6H); 6.10 (1H); 6.75 (2H); 6.91 (4H); 7.05 (4H); 7.59 (2H); 7.65 (1H); 8.01 (1H); 8.14 (1H). Elemental analysis, theoretical values for JYL-SQ5 ($C_{36}H_{62}N_2O_8S$) (%): C, 72.86; H, 6.77; N, 3.03; S, 3.47. Experimental values (%): C, 72.07; H, 7.07; N, 2.86; S, 3.45.

The Second Synthesis Example

The second synthesis example is used to illustrate the synthesis of a compound according to another embodiment of this invention. This compound is represented as DTE-dye.

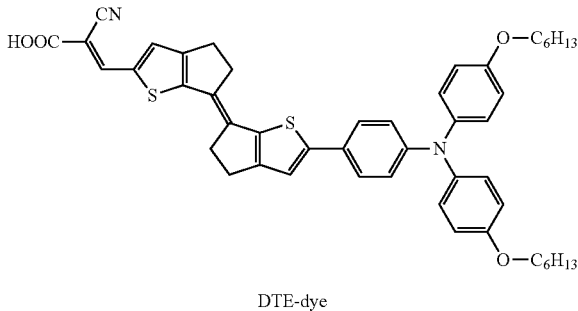

DTE-dye

DTE-dye is a compound with the structure of the formula (2) when six "G" represent hydrogen (—H) and a remained "G" connected closely to the sulfur atom represents the formula (54), and "E" in the formula (54) represents the formula (85), wherein m=0 and p=0, and $R_2$ represents —$CO_6H_{13}$; "D" in the formula (2) represents the formula (77), wherein "Z" represents hydrogen (—H).

The synthetic scheme for preparing DTE-dye is presented as the following:

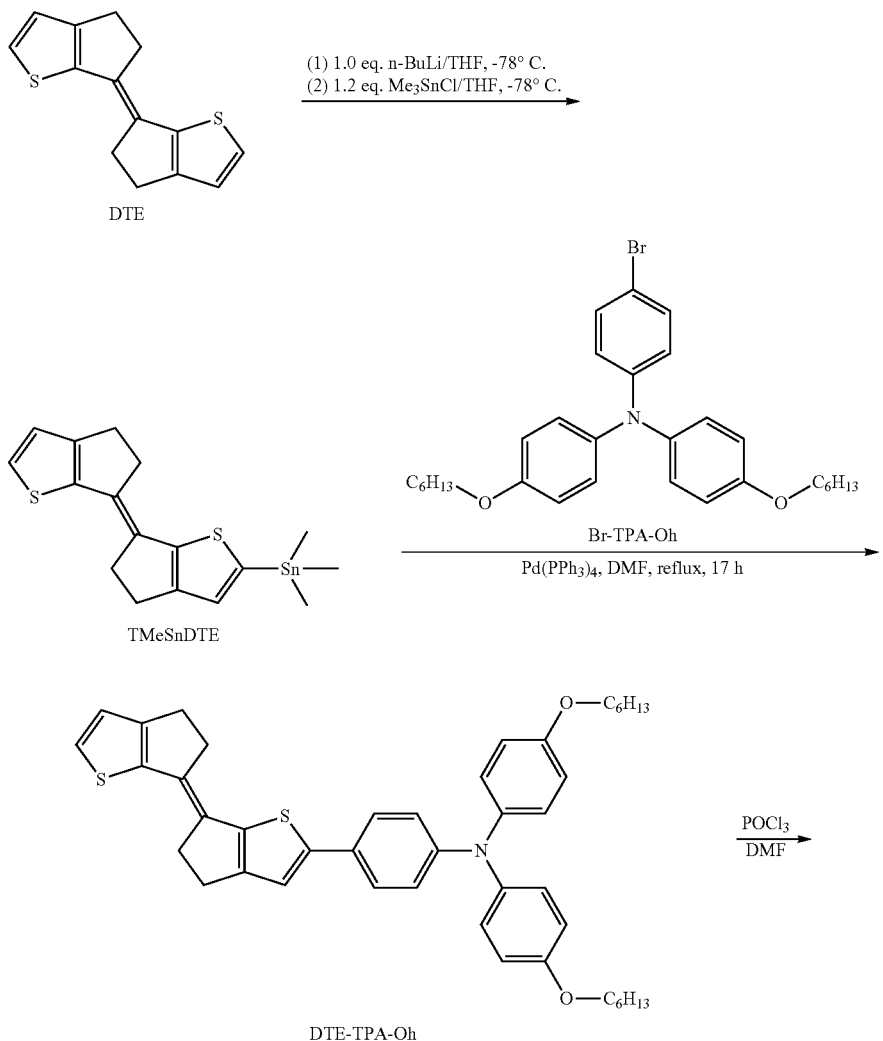

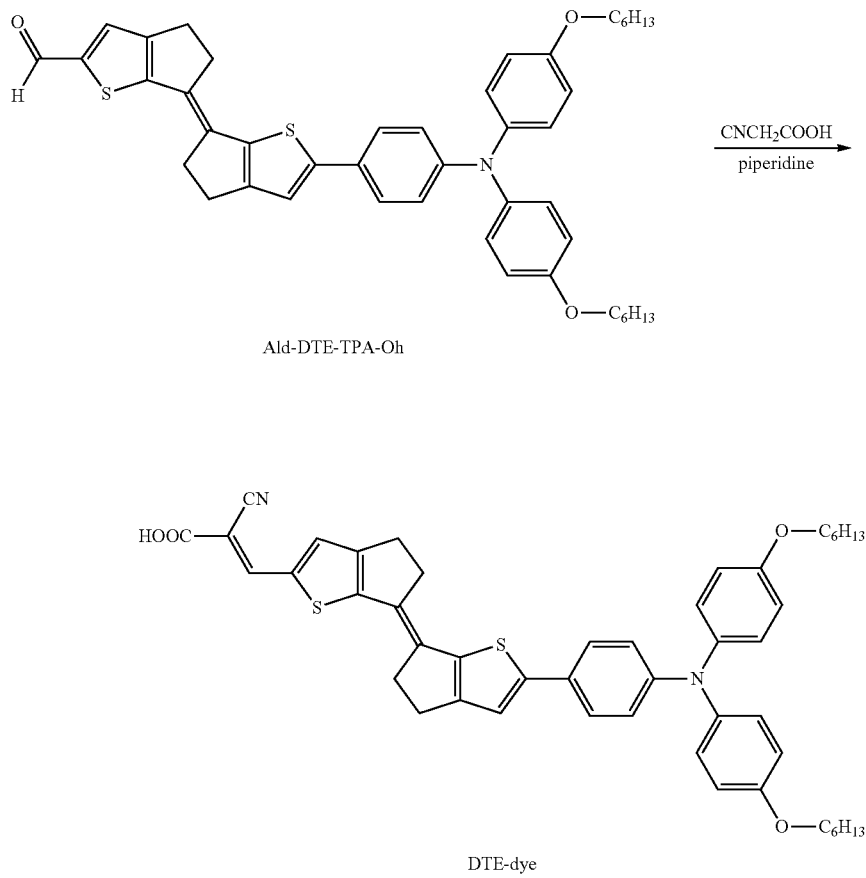

Ald-DTE-TPA-Oh

DTE-dye

First, 1.66 g DTE (the synthetic method can be referred to J. Roncali, C. T. Gautier, E. H. Elandaloussi, P. Frke, J. Chem. Soc., Chem. Commun., 1994, 2249.) was put in a round-bottom flask, followed by adding 250 ml of anhydrous tetrahydrofuran to dissolve the DTE. The temperature of the solution was controlled at −78° C. Then 2.7 ml (6.79 mmol) n-butyl-lithium (n-BuLi) (2.5 M in hexane) was injected slowly into the DTE solution. After n-BuLi was added, the temperature of the solution was allowed to return to the room temperature, and then stirred for another two hours. The temperature of the solution was decreased to −78° C. again and 1.65 g (8.15 mmol) trimethylstannane chloride (Me$_3$SnCl) dissolved in trace amount of anhydrous tetrahydrofuran was injected into the solution. After the temperature of the solution returned to the room temperature, the solution was stirred for 10 hours. De-ionized water was added to terminate the reaction, and CHCl$_3$ was used to extract the product. The organic layer was collected and the solvent was removed with a rotary evaporator to obtain the intermediate, coded TMeSnDTE. Without further purification, TMeSnDTE was mixed with 2.79 g Br-TPA-Oh (the synthesis method can be referred to G Zhang, H. Bala, Y. Cheng, D. Shi, X. Lv, Q. Yu, P. Wang. Chem. Commun., 2009, 2198.) and 160 ml anhydrous dimethylformamide. In addition, 0.34 g (0.289 mmol) tetrakis(triphenyl-phosphine) palladium was added as a catalyst. The mixture was heated at 150° C. for 72 hours and cooled to the room temperature, then 5 wt % of ammonium chloride aqueous solution was added to terminate the reaction. Chloroform was used to extract the product. The collected organic layer was dried over MgSO$_4$. After removing the solvent with a rotary evaporator, the crude product was purified further by chromatography to obtain the intermediate, coded DET-TPA-Oh. $^1$H-NMR (300 MHz, $\delta_H$/ppm in CDCl$_3$): 0.90 (6H); 1.34 (8H); 1.45 (4H); 1.76 (4H); 3.26-2.97 (8H); 3.91 (4H); 6.81 (4H); 6.88 (3H); 6.99 (1H); 7.05 (4H); 7.26 (1H); 7.34 (2H).

Thereafter, DET-TPA-Oh was dissolved in an appropriate volume of anhydrous dimethylformamide, followed by adding anhydrous phosphoryl chloride. The resulting solution was stirred for several hours, and then the solvent was removed to obtain the intermediate, coded Ald-DET-TPA-Oh. Finally, Ald-DET-TPA-Oh was dissolved in an appropriate volume of piperidine, and then cyanoacetic acid (CNCH$_2$COOH) was added to produce the final product (the synthesis method can be referred to C. Kim, H. Choi, S. Kim, C. Baik, K. Song, M. S. Kang, S. O. Kang, J. Ko, J. Org. Chem., 2008, 73, 7072). $^1$H-NMR (300 MHz, $\delta_H$/ppm in DMSO-d6): 0.86 (6H); 1.22-1.36 (12H); 1.68 (4H); 3.05 (4H); 3.24 (4H); 3.93 (4H); 6.75 (2H); 6.91 (4H); 7.03 (4H); 7.30 (1H); 7.47 (2H); 7.50 (1H); 7.94 (1H).

The Third Synthesis Example

The third synthesis example is used to illustrate the synthesis of a compound according to another embodiment of this invention. This compound is represented as SJW-B17.

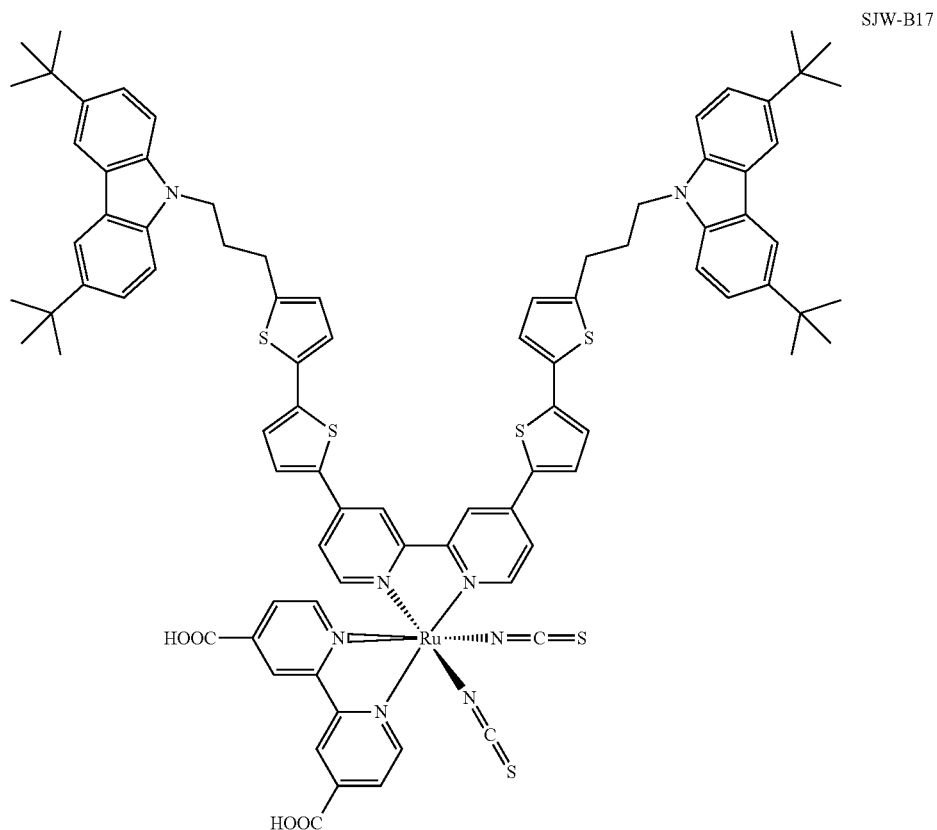

SJW-B17

SJW-B17 is a compound with a structure of the formula (3), and "G" represents the formula (51), wherein "X" in the formula (51) represents sulfur (S) atom, n=2, one of "E" represents the formula (84), and the other two "E" represent the formula (43). In the formula (84), m=3, p=0, and $R_2$ represents —$C_4H_9$; "D" in the formula (3) represents the formula (74) wherein "Z" represents hydrogen (—H).

The synthetic scheme for preparing SJW-B17-dye is presented as the following:

Scheme 3: Synthesis of SJW-B17

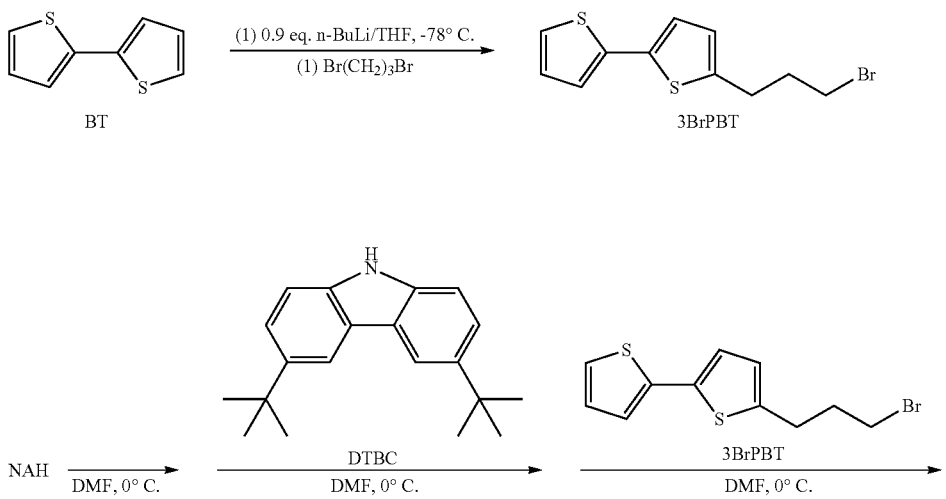

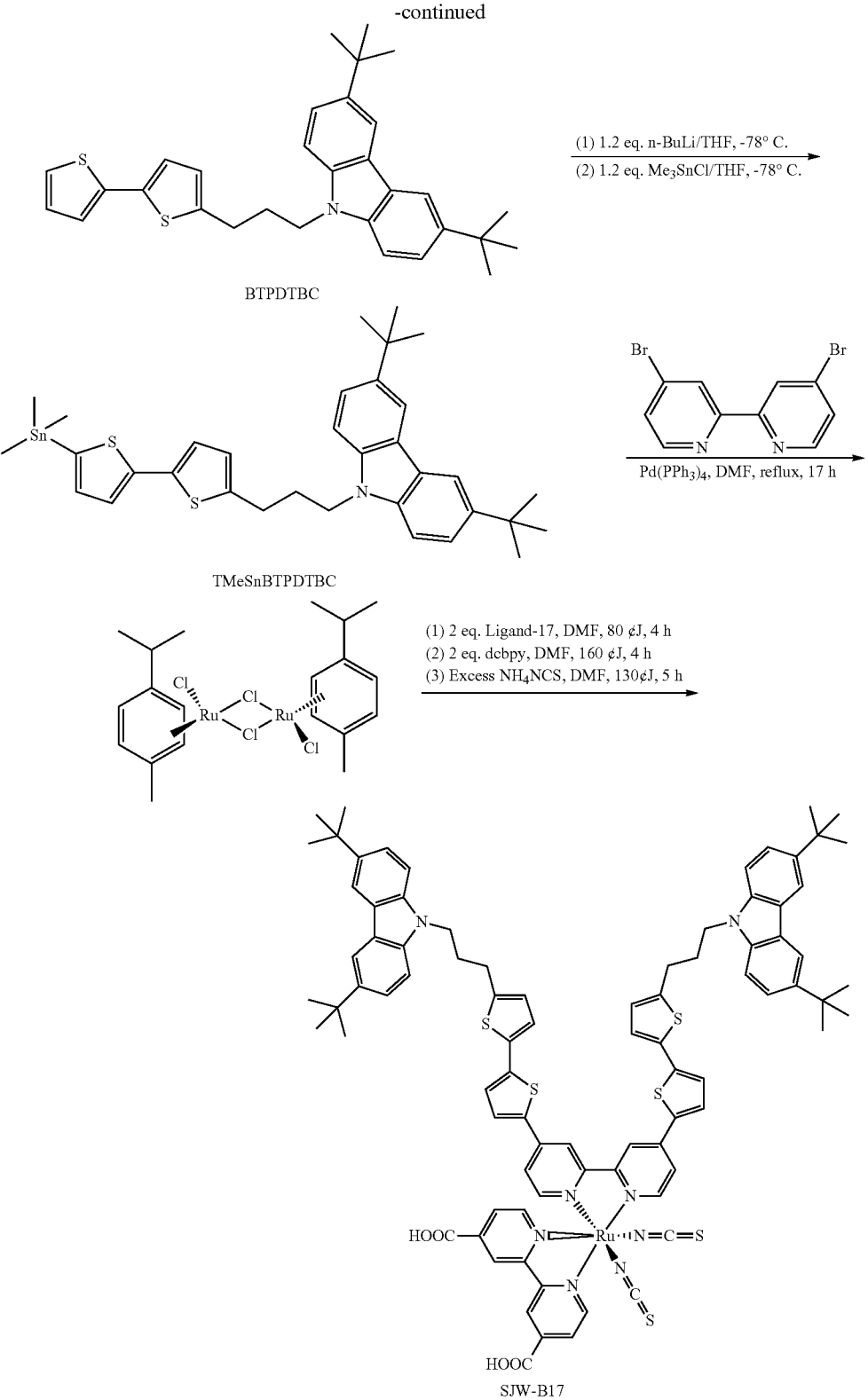

First, 4 g (25 mmol) bithiophene was put in a round-bottom flask, followed by adding 60 ml anhydrous tetrahydrofuran to dissolve the bithiophene. The temperature of the solution was lowered to −78° C. and then 8.8 ml (22 mmol) n-butyl-lithium (n-BuLi) (2.5 M in hexane) was injected slowly into the solution. Let the temperature of the reaction solution returned to the room temperature automatically then stirred for another 1 hour. The temperature of the solution was lowered to −78° C. again and then 5 g (25 mmol) 1,3-dibromopropane was injected into the solution. After the temperature of the solution returned to the room temperature, the solution was stirred for 10 hours. Ammonium chloride aqueous solution was added to terminate the reaction and dichloromethane was used to extract the product. The resulting crude product was purified using chromatography to afford 4.22 g intermediate, 5-(3-bromopropyl)-2,2'-bithiophene, coded 3BrPBT. $^1$H-NMR (300 MHz, $\delta_H$/ppm in CDCl$_3$): 2.28 (2H); 3.02 (2H); 3.49 (2H); 6.75 (1H); 7.01 (2H); 7.17 (1H); 7.20 (1H).

0.93 g (38.8 mmol) of sodium hydride was dissolved in 25 ml dimethylformamide. The temperature of the solution was lowered to 0° C. by using an ice-bath, and then a solution containing 5.15 g (18.4 mmol) 3,6-di-tert-butyl-9H-carbazole dissolved in 30 ml dimethylformamide was added slowly. The mixture was stirred for 1 hour at 0° C. and then 4.22 g (18.4 mmol) 3BrPBT dissolved in 30 ml dimethylformamide was added into it. Let the reaction mixture returned to the room temperature then stirred for another 8 hours. An ammonium chloride aqueous solution was added to terminate the reaction. Dichloromethane was used to extract the product. After purification, 6.56 g of an intermediate product coded BTPDTBC, (9-(3-(2,2'-bithiophen-5-yl)propyl)-3,6-di-tert-butyl-9H-carbazole) was obtained. $^1$H-NMR (300 MHz, $\delta_H$/ppm in CDCl$_3$): 1.46 (18H); 2.32 (2H); 2.91 (2H); 4.35 (2H); 6.69 (1H); 7.01 (2H); 7.11 (1H); 7.19 (1H); 7.29 (2H); 7.52 (2H); 8.10 (2H).

6.56 g (10.1 mmol) BTPDTBC was dissolved in 70 ml anhydrous tetrahydrofuran. The temperature of the solution was lowered to −78° C., and then 6.5 ml (16.25 mmol) n-butyl-lithium (n-BuLi) (2.5 M in hexane) was added slowly. Let the solution returned to the room temperature, then stirred for 2 hours. Decreasing the temperature of the solution to −78° C. again, followed by adding 3.67 g (18.4 mmol) trimethylstannane chloride (Me$_3$SnCl) dissolved in 30 ml of anhydrous tetrahydrofuran. Let the temperature of the reaction mixture returned to the room temperature and stirred for another 12 hours. De-ionized water was added to terminate the reaction and the product was extracted with dichloromethane. The organic layer was collected and the solvent was removed by a rotary evaporator to obtain 8.84 g (13.6 mmol) of the crude product, coded TMeSnBTPDTBC, (3,6-di-tert-butyl-9-(3-(5'-(trimethyl-stannyl)-2,2'-bi-thiophen-5-yl)propyl)-9H-carbazole). The 8.84 g crude product, TMeSnBTPDTBC and 1.93 g (6.17 mmole) 4-4'-dibromo-2,2'-bipyridine (the synthesis method can be referred to I. Murase, Nippon Kagaku Zasshi, 1956, 77, 682; G Mnerker, F. H. Case, J. Am. Chem. Soc., 1958, 80, 2745; and D. Wenkert, R. B. Woodward, J. Org. Chem., 1983, 48, 283.) were dissolved in 60 ml dimethylformamide, follow by adding 0.95 g of tetrakis(triphenylphosphine)-palladium as a catalyst. The reaction mixture was refluxed for 72 hours. When the temperature of the solution returned to the room temperature, a saturated ammonium chloride aqueous solution was added and stirred for 10 minutes to terminate the reaction. Chloroform was used to extract the product and the organic layer was dried over MgSO$_4$. After purification with a Soxhlet extractor to obtain the product, coded Ligand-17. $^1$H-NMR (300 MHz, $\delta_H$/ppm in CDCl$_3$): 1.46 (36H); 2.34 (4H); 2.93 (4H); 4.37 (4H); 6.73 (2H); 7.09 (2H); 7.24 (2H); 7.30 (4H); 7.57 (8H); 8.11 (4H); 8.63 (2H); 8.68 (2H).

4.2 g of Ligand-17 and 1.15 g [RuCl$_2$ (p-cymene)] 2 were dissolved in 160 ml of anhydrous dimethylformamide. The reaction solution was heated at 80° C. for 4 hours, and then 0.90 g 4,4'-dicarboxylic acid-2,2'-bipyridine (dcbpy) was added. The solution mixture was refluxed at 160° C. for 4 hours, and then an excessive amount of ammonium thiocyanate was added to the solution, at the same time the temperature was lowered to 130° C. and reacted for 5 hours. (The detailed synthetic and purification procedures can be referred to C. Y. Chen, S. J. Wu, C. G Wu, J. G Chen, K. C. Ho, Angew. Chem. Int. Ed., 2006, 45, 5822.). After purification, 0.78 g of the final product, SJW-B17, was obtained. $^1$H-NMR (500 MHz, $\delta_H$/ppm in DMSO-d6): 1.39 (36H); 2.11 (4H); 2.87 (4H); 4.41 (4H); 6.83 (1H); 6.90 (1H); 7.22 (1H); 7.32 (2H); 7.46 (10H); 7.62 (2H); 7.90 (1H); 7.99 (1H); 8.18 (6H); 8.30 (1H); 8.88 (1H); 8.94 (1H); 9.03 (1H); 9.10 (1H); 9.16 (1H); 9.43 (1H). Mass analysis, calculated value: m/z=1615.45 ([M]$^+$). Found (LRMS-FAB): m/z=1614.24 (m) ([M]$^+$).

The Fourth Synthesis Example

The fourth synthesis example is used to illustrate the synthesis of a compound according to another embodiment of this invention. This compound is represented as SJW-B18.

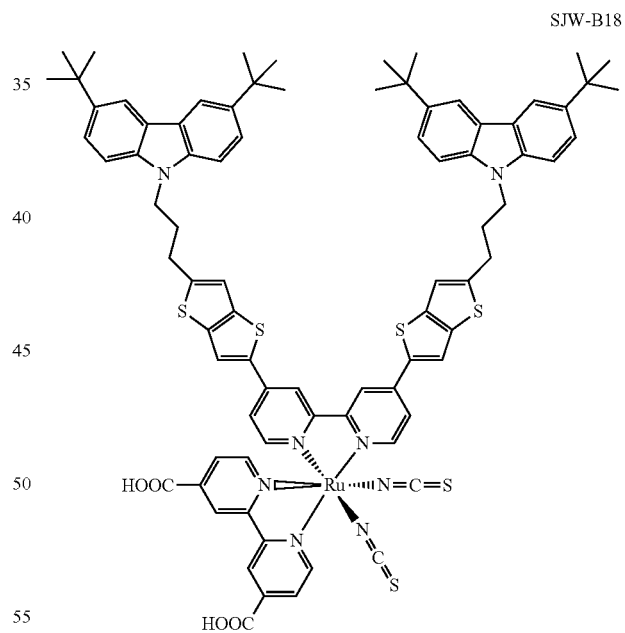

SJW-B18

SJW-B18 is a compound with a structure of the formula (3), wherein "G" represents the formula (63), and X in the formula (63) represents sulfur (S) atom, and one of E represents the formula (84), another E and R$_2$ represent the formula (43). In the formula (84), m=3, p=0, and R$_2$ represents —C$_4$H$_9$; D in the formula (3) represents the formula (74), wherein Z represents hydrogen (—H).

The synthetic scheme for preparing SJW-B17-dye is presented as the following:
Scheme 4: Synthesis of SJW-B18
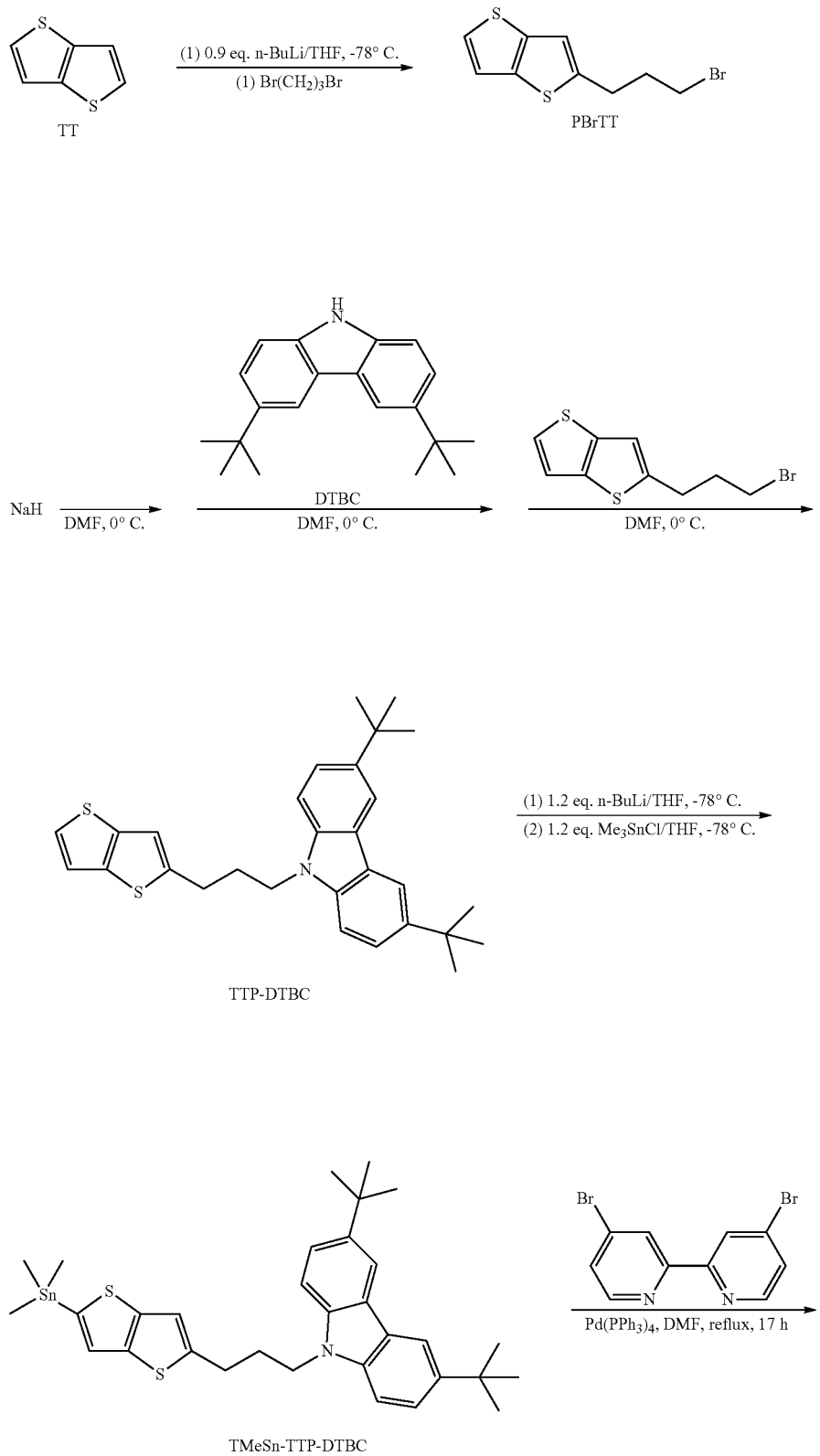

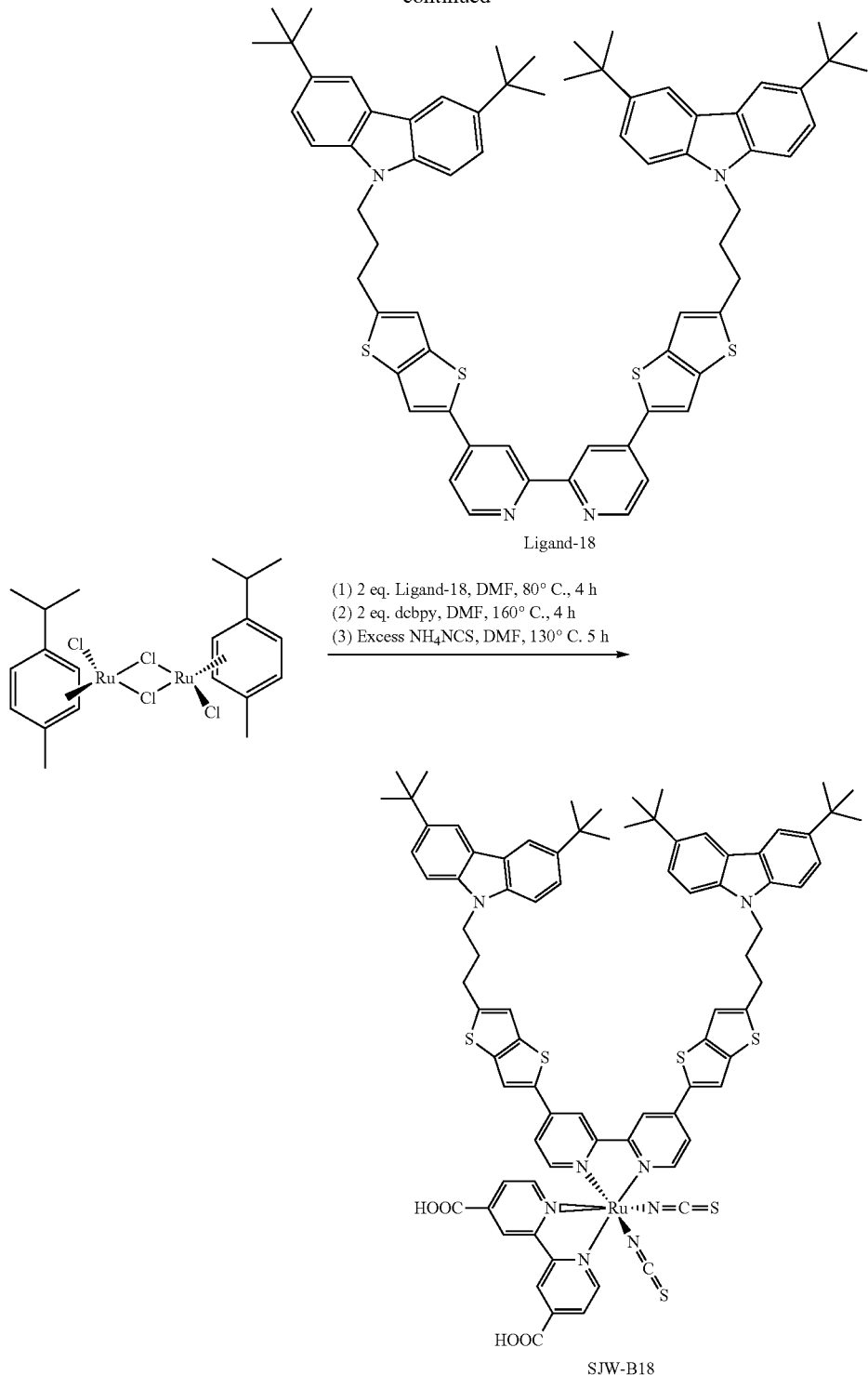

Ligand-18

(1) 2 eq. Ligand-18, DMF, 80° C., 4 h
(2) 2 eq. dcbpy, DMF, 160° C., 4 h
(3) Excess NH₄NCS, DMF, 130° C. 5 h

SJW-B18

The synthesis of starting material (thieno[3,2-b]thiophene) can be referred to P. Leriche, J. M. Raimundo, M. Turbiez, V. Monroche, M. Allain, F. Xavier Sauvage, J. Roncali, P. Frère, P. J. Skabara, J. Mater. Chem., 2003, 13, 1324. The synthetic procedures for the intermediates and Ligand-18 are the same as those for the preparation of Ligand-17 disclosed previously. Structural identification of the intermediates and Ligand-18 is described as the following.

(1) $^1$H-NMR spectrum of intermediate coded PBrTT (300 MHz, $\delta_H$/ppm in CDCl$_3$): 2.25 (2H); 3.07 (2H); 3.46 (2H); 7.02 (1H); 7.18 (1H); 7.30 (1H).

(2) $^1$H-NMR spectrum of intermediate coded TTP-DTBC (300 MHz, $\delta_H$/ppm in CDCl$_3$): 1.44 (18H); 2.28 (2H); 2.95 (2H); 4.32 (2H); 6.93 (1H); 7.17 (1H); 7.24 (1H); 7.27 (2H); 7.48 (2H); 8.08 (2H).

(3) $^1$H-NMR spectrum of Ligand-18 (300 MHz, $\delta_H$/ppm in CDCl$_3$): 1.46 (36H); 2.35 (4H); 2.98 (4H); 4.35 (4H); 6.95 (2H); 7.26 (2H); 7.29 (2H); 7.49 (4H); 7.52 (2H); 7.78 (2H); 8.11 (4H); 8.66 (4H). After Ligand-18 was prepared, the final product (SJW-B18) can be obtained by using the same synthesis and purification procedures as those for preparing SJW-B17 described in the third synthesis example.

Figure 2:
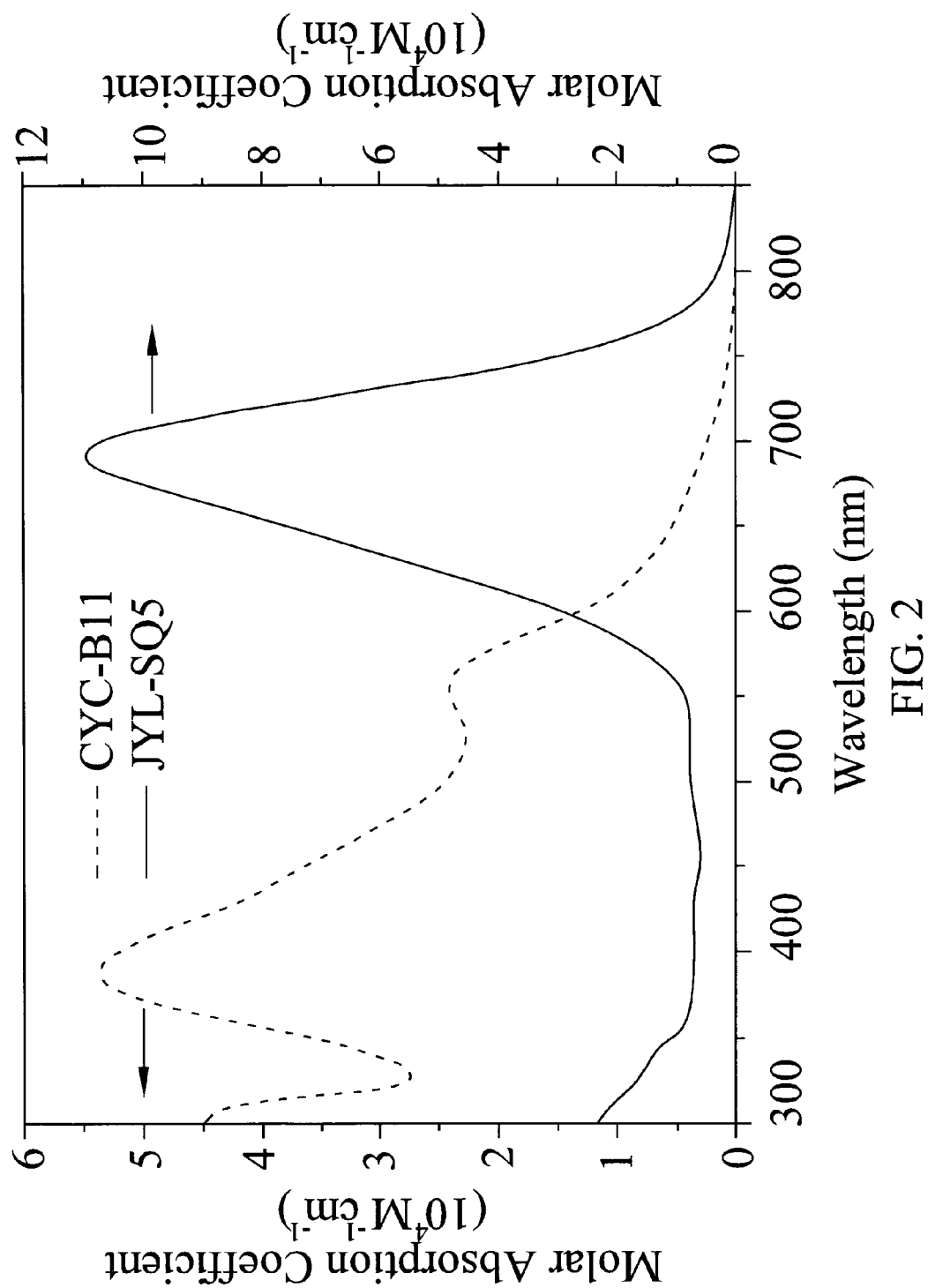
FIG. 2 is the absorption spectra of the photosensitizer dye (JYL-SQ5) of the present invention and the photosensitizer dye (CYC-B11) of the prior art.

Furthermore, the following description is directed to the method for measuring the absorption coefficient ($\epsilon$) of the photosensitizer dyes in the present invention. Comparisons between the absorption coefficients and the absorption maximum of JYL-SQ5 and SJW-B17 in the present invention and that of photosensitizer dyes in prior arts are also provided. According to the measuring method, photosensitizer dye solutions with known concentrations are prepared first. An appropriate amount of the solution is placed in a quartz cuvette, and then the quartz cuvette is put in the sample compartment of a UV/Vis Spectrophotometer for analyzing. The absorption coefficient can be calculated according to the Beer's low (A=$\epsilon$bc, A: absorbance; $\epsilon$: absorption coefficient; b: beam path; c: concentration of the sample). The absorption spectra of the photosensitizer dyes (JYL-SQ5 and SJW-B17) in the present invention and the conventional photosensitizer dye (N3) or CYC-B11 are shown in FIG. 1 and FIG. 2. The absorption coefficients of the photosensitizer dyes (JYL-SQ5 and SJW-B17) are compared with those of the various conventional dyes, and the results are summarized in Table 1.

In Table 1, the conventional photosensitizer dyes, "N3", "Black dye", "Z-910", "CYC-B11" and "SQ01" are respectively disclosed by "M. Grätzel, J. Photochem. A, 2004, 164, 3, M. K. Nazeeruddin et al., J. Am. Chem. Soc. 1993, 115, 6382", "M. K. Nazeeruddin et al., J. Am. Chem. Soc. 2001, 123, 1613", "P. Wang, et al., Adv. Mater. 2004, 16, 1806", "C. Y. Chen, M. Wang, J. Y. Li, N. Pootrakulchote, L. Alibabaei, C. Ngoc-le, J. D. Decoppet, J. H. Tsai, C. Grätzel, C. G Wu, S. M. Zakeeruddin & M. Grätzel, ACS Nano 2009, 3, 3103", and "J. H. Yum et al. J. Am. Chem. Soc. 2007, 129, 10320.".

TABLE 1

| Photosensitizer dye | Absorption maximum (nm) | The molar absorption coefficient of the absorption maximum (M$^{-1}$ cm$^{-1}$) |
|---|---|---|
| JYL-SQ5 | 691 | 109,600 |
| SJW-B17 | 552 | 22,400 |
| N3 | 530 | 14,500 |
| Black dye | 600 | 7,640 |
| Z910 | 543 | 16,850 |
| CYC-B11 | 553 | 24,200 |
| SQ01 | 636 | 158,500 |

As shown in Table 1, the absorption maximum of JYL-SQ5 in the present invention is longer than those of the conventional photosensitizer dyes, and the absorption coefficient of JYL-SQ5 is higher than those of most conventional photosensitizer dyes. The absorption coefficient of SJW-B17 in the present invention is close to those of the conventional photosensitizer dyes, and the absorption maximum of SJW-B17 is also longer than those of the conventional photosensitizer dyes. Accordingly, the organic and inorganic photosensitizer dyes of the present invention have the aforementioned specific groups. That is, "A" represents one of the formulas (4) to (15); "B" represents one of the formulas (16) to (42); "G" represents independently one of the formulas (43) to (73); "D" represents independently one of the formulas (74) to (83); and "E" represents independently one of the formulas (43) to (49) or (84) to (97). Therefore, the organic and inorganic photosensitizer dyes of the present invention have higher molar absorption coefficient ($\epsilon$). The organic and inorganic photosensitizer dyes of the present invention can effectively absorb the photons of the visible light and the parts of the near infrared light in sunlight, and have higher absorption capacity than those in the prior art. Therefore, dye-sensitized solar cell based on the organic and inorganic photosensitizer dyes of the present invention can potentially have higher efficiency for converting sunlight to electricity.

Additionally, comparing the absorption spectrum of JYL-SQ5 with that of the ruthenium (Ru) complex photosensitizer dye such as "CYC-B11", JYL-SQ5 can compensate the insufficient absorption at the far-red region of the ruthenium complex photosensitizer dye. Therefore, JYL-SQ5 can be a co-dye of the Ru based photosensitizer to increase the conversion efficiency of the dye-sensitized solar cells. To sum up the above results, dye-sensitized solar cells sensitized with the organic and inorganic photosensitizer dyes of the present invention will have a good performance.

Dye-sensitized solar cells fabricated by using JYL-SQ5 and SJW-B17 as the photosensitizer are shown as follows. First, a titanium dioxide (TiO$_2$) electrode is soaked in a JYL-SQ5-containing solution or a SJW-B17-containing solution for a while. JYL-SQ5 or SJW-B17 attached on the surface of the TiO$_2$ electrode by a self-assembly manner. Thereafter, the TiO$_2$ electrode is removed from the dye solution and rinsed with a solvent, dried and then covered with a counter electrode. The two electrodes are sealed with an epoxy and the intervening space between two electrodes is filled with an electrolyte solution by injection the electrolyte solution through the hole made on the counter electrode. After sealing the injection opening, the preparation of a dye-sensitized solar cell is completed. Subsequently the voltage, current density, filling factor and conversion efficiency of the dye-sensitized solar cells based on JYL-SQ5 and SJW-B17 are measured under the AM 1.5 (light intensity of 100 mW/cm$^2$) and the preliminary results are summarized in Table 2.

TABLE 2

| Photosensitizer dye | Short circuit current density, Jsc (mA/cm$^2$) | Open circuit voltage, Voc (mV) | Fill factor, FF | Energy conversion efficiency, $\eta$ (%) |
|---|---|---|---|---|
| JYL-SQ5 | 9.34 | 389 | 0.60 | 2.19 |
| SJW-B17 | 13.23 | 640 | 0.57 | 4.90 |

As shown in Table 2, by using JYL-SQ5 or SJW-B17 as a dye to fabricate the dye-sensitized solar cell, the conversion efficiency thereof is about 2.19% and 4.90%, respectively. Thus, the organic and inorganic photosensitizer dyes of the present invention have excellent potential to be applied in the dye-sensitized solar cell.

Figure 3:
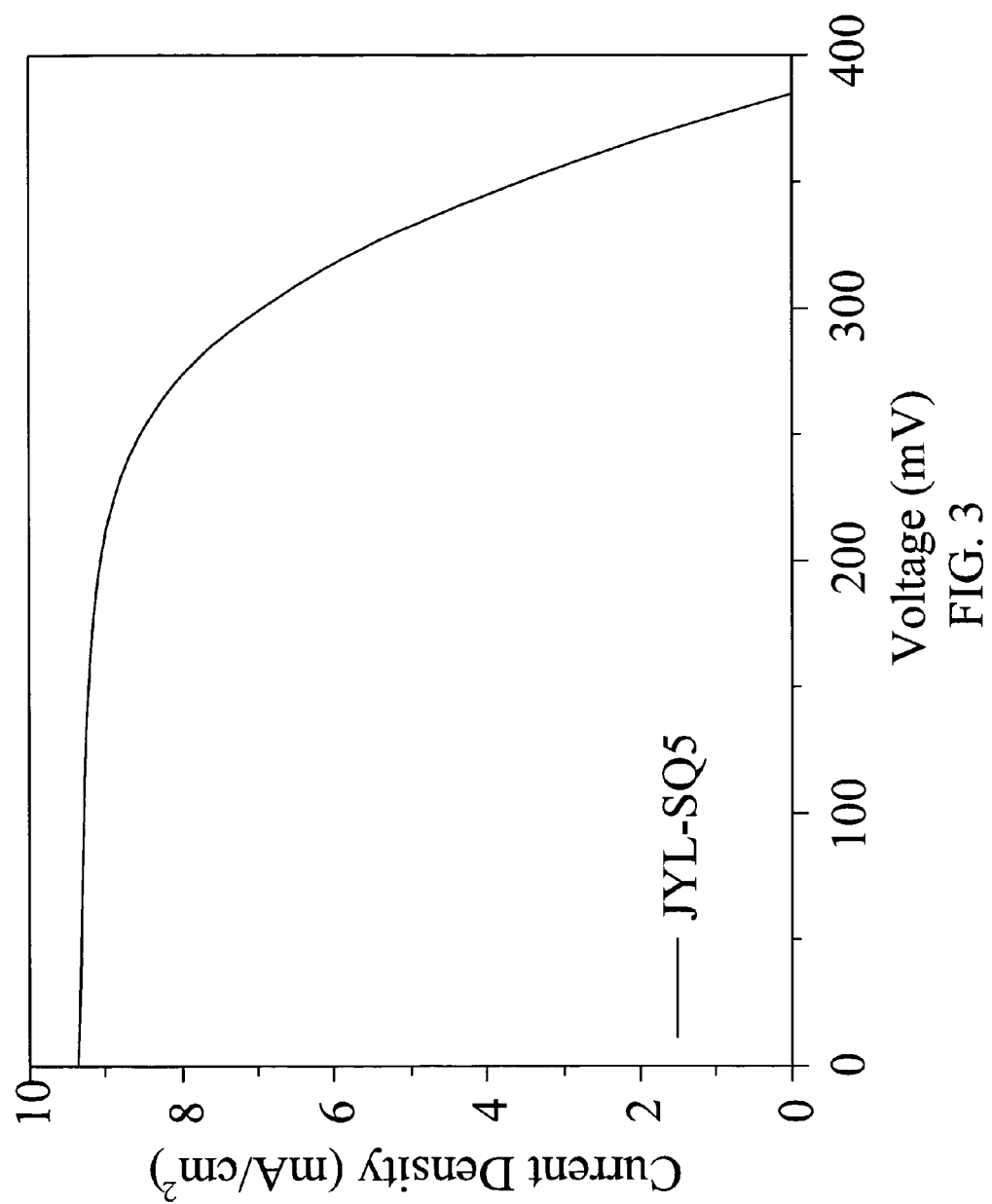
FIG. 3 is a current-potential curve of a dye-sensitized solar cell based on JYL-SQ5 of the present invention.
Figure 4:
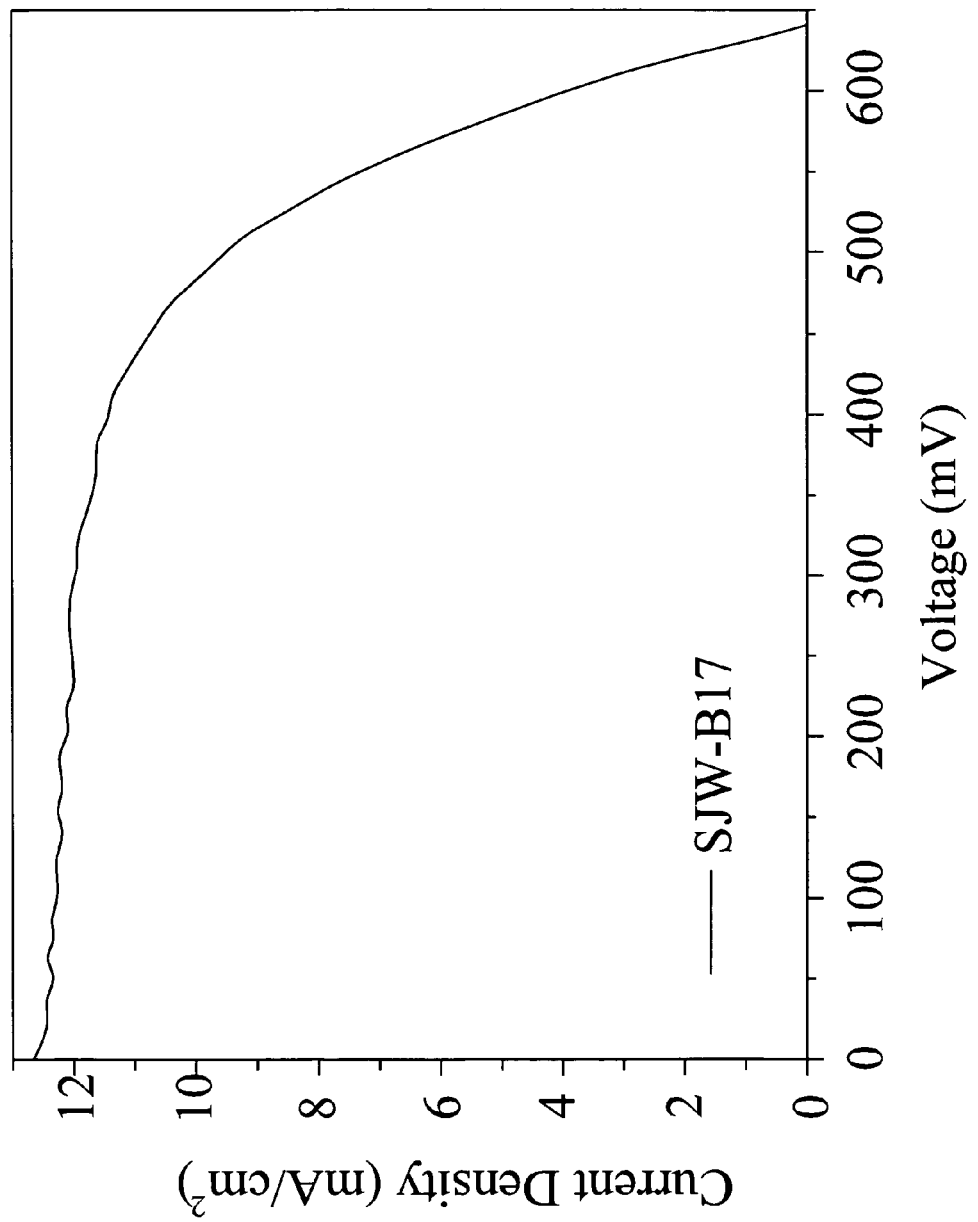
FIG. 4 is a current-potential curve of a dye-sensitized solar cell based on SJW-B17 of the present invention.

The series of the organic and inorganic photosensitizer dyes, the formulas (1) to (3), according to the present invention have the specific groups as set forth. That is, "A" represents one of the formulas (4) to (15); "B" represents one of the formulas (16) to (42); "G" represents independently one of the formulas (43) to (73); "D" represents independently one of the formulas (74) to (83); and "E" represents independently one of the formulas (43) to (49) or (84) to (97). Thus, the series of the organic and inorganic photosensitizer dyes of the present invention have good light absorption capacity and high molar absorption coefficient ($\epsilon$). The organic and inorganic photosensitizer dyes of the present invention can effectively absorb the photons of the visible light and the parts of the near infrared light in sunlight. When the organic and inorganic photosensitizer dyes of the present invention are applied to dye-sensitized solar cells, the dye-sensitized solar cells can potentially have higher conversion efficiency. In the present embodiment, JYL-SQ5 or SJW-B17 is used as the photosensitizer in dye-sensitized solar cells, and the current-potential curve of the dye-sensitized solar cells based on JYL-SQ5 or SJW-B17 are shown in FIG. 3 and FIG. 4, respectively. The results illustrate that JYL-SQ5 and SJW-B17 can be truly applied to dye-sensitized solar cells.

The present invention has been described with some preferred embodiments thereof and it is understood that many changes or modifications in the described embodiments can be carried out without departing from the scope and the spirit of the invention that is intended to be limited only by the appended claims.

What is claimed is:

1. An organic and inorganic photosensitizer dye applied to dye-sensitized solar cells, comprising one of the following formula (3):

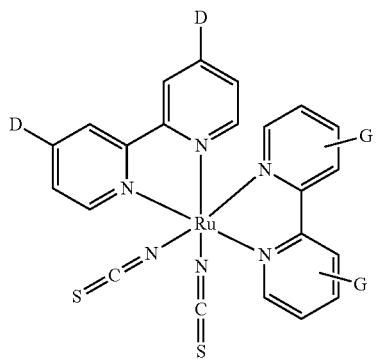
(3)

wherein G represents independently one of the formulas (46) to (73);

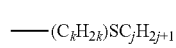
(46)

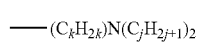
(47)

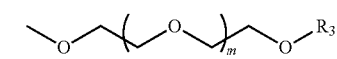
(48)

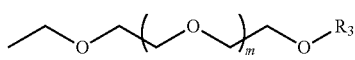
(49)

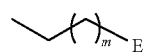
(50)

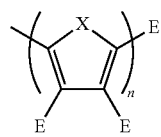
(51)

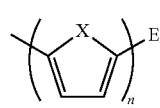
(52)

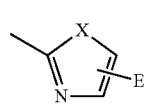
(53)

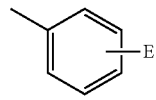
(54)

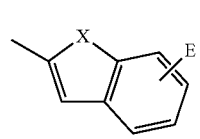
(55)

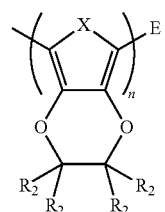
(56)

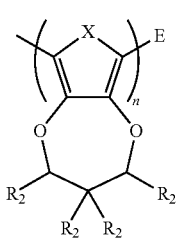
(57)

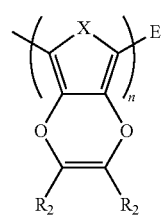
(58)

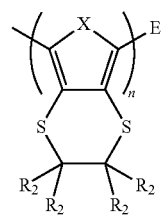
(59)

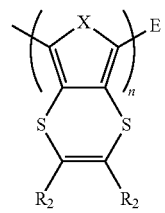
(60)

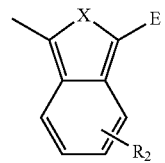
(61)

wherein D represents independently one of the formulas (74) to (83);

-continued
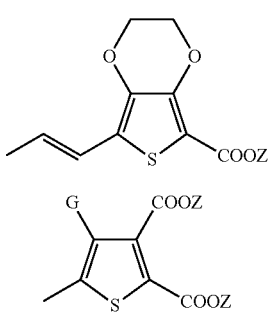
(82)
(83)
wherein E represents independently one of the formulas (46) to (49) or (84) to (97);
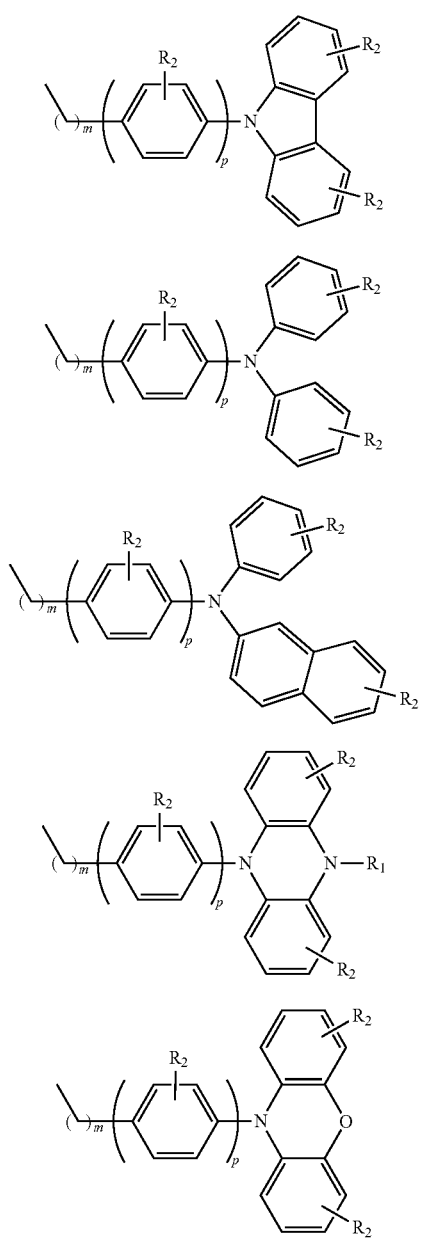
(84)
(85)
(86)
(87)
(88)
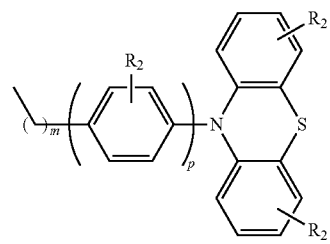
(89)
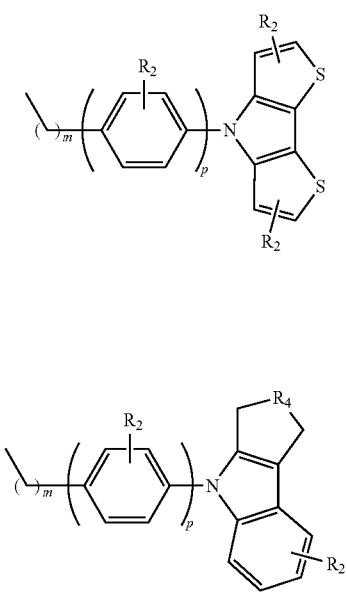
(90)
(91)
(92)
(93)

-continued

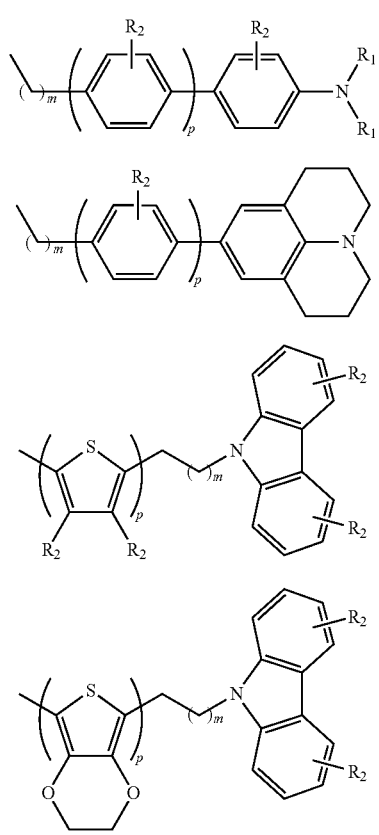

wherein Z represents independently hydrogen (H), lithium (Li), sodium (Na), potassium (K) or a quaternary ammonium salt shown in the following formula (98);

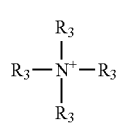

wherein X in the formulas (51) to (53) and (55) to (66) represents independently one of the sulfur (S), an amino group (N—R; R represents $C_qH_{2q+1}$ (q=1 to 20)), oxygen (O) or selenium (Se); j=1 to 20 in the formulas (46) to (47); k=0 to 20 in the formulas (46) to (47); m=1 to 10 in the formulas (84) to (97); n=1 to 4 in the formulas (51) to (52) and in formulas (56) to (60); p=0 to 2 in the formulas (84) to (97); $R_1$ in the formulas (67), (70), (72) to (73), (87), (93) and (94) represents independently $C_xH_{2x+1}$, $(C_yH_{2y})$—$OC_xH_{2x+1}$, $(C_yH_{2y})$—$SC_xH_{2x+1}$, $(C_yH_{2y})$—$N(C_xH_{2x+1})_2$ (x=1 to 20; y=1 to 20) or the formulas (49) to (50); $R_2$ in the formulas (56) to (61), (63) to (65), (67) to (69), (71) and (84) to (97) represents independently hydrogen (H), $C_xH_{2x+1}$, $(C_zH_{2z})$—$OC_xH_{2x+1}$, $(C_zH_{2z})$—$SC_xH_{2x+1}$, $(C_zH_{2z})$—$N(CH_xH_{2x+1})_2$ (x=1 to 20; z=0 to 20) or the formulas (48) to (50); $R_3$ in the formulas (48), (49) and (98) represents independently hydrogen (H) or $C_xH_{2x+1}$, (x=1 to 20); and $R_4$ in the formula (91) represents $C_wH_{2w}$, (w=1 to 2).

2. The organic and inorganic photosensitizer dye as claimed in claim 1, wherein when D in the formula (3) represents one of the formulas (74) to (76) or (79) to (82) and G in the formula (3) represents one of the formulas (51) to (66), E in the formulas (51) to (66) do not represent one of the formulas (46) to (49); and when E in the formulas (51) to (66) represents one of the formulas (84) to (95).

3. The organic and inorganic photosensitizer dye as claimed in claim 1, wherein when D in the formula (3) represents one of the formulas (77) or (78) and Z in the formulas (77) or (78) represents H, G in the formula (3) do not represent one of the formulas (46) to (47); when G represents one of the formulas (51) to (55) and E in the formulas (51) to (55) represents one of the formulas (84), (88) or (89).

4. The organic and inorganic photosensitizer dye as claimed in claim 1, wherein the structures of the organic and inorganic photosensitizer dye are shown as the following formulas (118) to (119):

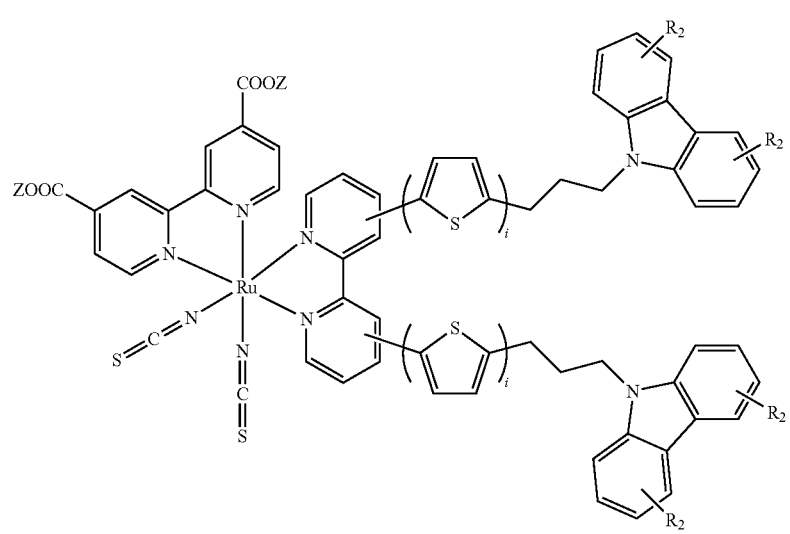

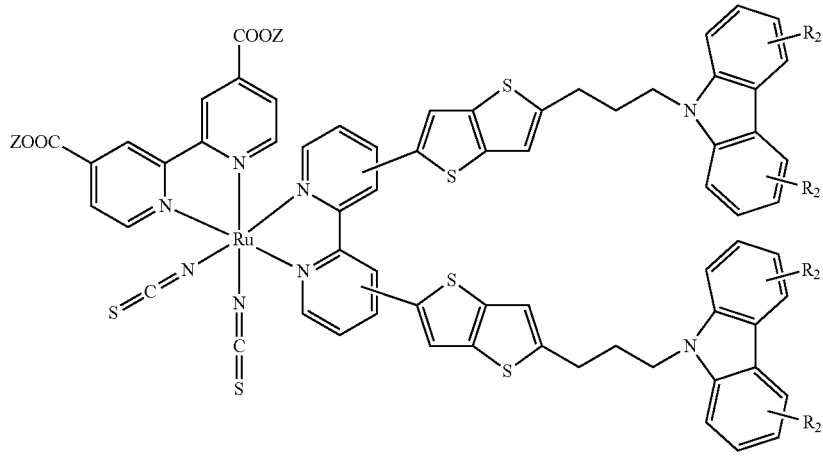

(119)

wherein i represents independently 1 to 3 in the formula (118); $R_2$ in the formulas (118) to (119) represents independently one of H, $-C_xH_{2x+1}$, $-(C_zH_{2z})-OC_xH_{2x+1}$, $-(C_zH_{2z})-SC_xH_{2x+1}$, $-(C_zH_{2z})-N(C_xH_{2x+1})_2$ (x=1~20; z=0~20) or the formulas (48) to (50); and Z in the formulas (118) to (119) represents independently H, lithium (Li), sodium (Na), potassium (K) or the quaternary ammonium salt as shown in the formula (98);

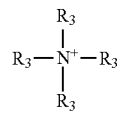

(98)

wherein $R_3$ in the formula (98) represents independently hydrogen (—H) or $-C_xH_{2x+1}$ (x=1~20).

* * * * *

UNITED STATES PATENT AND TRADEMARK OFFICE
CERTIFICATE OF CORRECTION

PATENT NO. : 8,404,842 B2  
APPLICATION NO. : 12/924777  
DATED : March 26, 2013  
INVENTOR(S) : Chun-Guey Wu et al.

Page 1 of 1

It is certified that error appears in the above-identified patent and that said Letters Patent is hereby corrected as shown below:

On the title page, item [75]: the first inventor's name has been entered incorrectly as "Chn-Guey Wu", the correct name is "Chun-Guey Wu"

Signed and Sealed this
Seventeenth Day of December, 2013

Margaret A. Focarino
*Commissioner for Patents of the United States Patent and Trademark Office*

UNITED STATES PATENT AND TRADEMARK OFFICE
CERTIFICATE OF CORRECTION

PATENT NO.        : 8,404,842 B2                              Page 1 of 1
APPLICATION NO.   : 12/924777
DATED             : March 26, 2013
INVENTOR(S)       : Chun-Guey Wu et al.

It is certified that error appears in the above-identified patent and that said Letters Patent is hereby corrected as shown below:

In the Claims:

In claim 1, column 48, lines 15-16, the formula has been entered incorrectly: $(C_zH_{2z}) - N(CH_xH_{2x+1})_2$ The correct formula is: -- $(C_zH_{2z}) - N(C_xH_{2x+1})_2$ --

Signed and Sealed this
Sixth Day of May, 2014

Michelle K. Lee
*Deputy Director of the United States Patent and Trademark Office*